United States Patent
Agarwal et al.

(10) Patent No.: US 10,849,540 B2
(45) Date of Patent: Dec. 1, 2020

(54) BIOSENSOR DEVICE TO TARGET ANALYTES IN SITU, IN VIVO, AND/OR IN REAL TIME, AND METHODS OF MAKING AND USING THE SAME

(71) Applicant: THE UNIVERSITY OF TOLEDO, Toledo, OH (US)

(72) Inventors: Anand K. Agarwal, Toledo, OH (US); Vijay K. Goel, Toledo, OH (US); Dong-Shik Kim, Toledo, OH (US); Do Young Yoon, Toledo, OH (US); Boren Lin, Toledo, OH (US); Hamid Feyzizarnagh, Toledo, OH (US)

(73) Assignee: The University of Toledo, Toledo, OH (US)

( * ) Notice: Subject to any disclaimer, the term of this patent is extended or adjusted under 35 U.S.C. 154(b) by 844 days.

(21) Appl. No.: 14/774,499

(22) PCT Filed: Mar. 11, 2014

(86) PCT No.: PCT/US2014/023126
§ 371 (c)(1),
(2) Date: Sep. 10, 2015

(87) PCT Pub. No.: WO2014/164654
PCT Pub. Date: Oct. 9, 2014

(65) Prior Publication Data
US 2016/0022185 A1    Jan. 28, 2016

Related U.S. Application Data

(60) Provisional application No. 61/775,939, filed on Mar. 11, 2013.

(51) Int. Cl.
*A61B 5/1473* (2006.01)
*G01N 33/543* (2006.01)
(Continued)

(52) U.S. Cl.
CPC ...... *A61B 5/14735* (2013.01); *A61B 5/14546* (2013.01); *A61B 5/4547* (2013.01);
(Continued)

(58) Field of Classification Search
None
See application file for complete search history.

(56) References Cited

U.S. PATENT DOCUMENTS

| 4,209,585 A | 6/1980 | Lloyd et al. |
| 4,267,270 A | 5/1981 | Stout |

(Continued)

FOREIGN PATENT DOCUMENTS

| CN | 1443307 A | 9/2003 |
| CN | 101432625 A | 5/2009 |

OTHER PUBLICATIONS

Carrara et al., "Fully Integrated Biochip Platforms for Advanced Healthcare", Sensors, 2012, vol. 12, pp. 11013-11060.

(Continued)

*Primary Examiner* — Jacqueline Cheng
*Assistant Examiner* — Jairo H Portillo
(74) *Attorney, Agent, or Firm* — MacMillan, Sobanski & Todd, LLC

(57) ABSTRACT

A biosensor device for the real-time detection of a target analyte includes a receptor component operatively connected to a transducer component which is adapted to interpret and transmit a detectable signal. The receptor component includes a sensing element capable of detecting and binding to at least one target analyte, and a self-assembled monolayer (SAM) layer. The SAM layer is positioned between and in contact with the sensing element and an electrode such that the sensing element, in the presence of the target analyte, causes a detectable signal capable of being transmitted to the electrode. The transducer (Continued)

component includes the electrode and microprocessor configured to screen noise and to pick up impedance change at a very low frequency range.

25 Claims, 13 Drawing Sheets

(51) Int. Cl.
    *G01N 33/569*     (2006.01)
    *A61B 5/145*     (2006.01)
    *A61B 5/00*     (2006.01)
    *G01N 27/327*     (2006.01)

(52) U.S. Cl.
    CPC ..... *G01N 27/3272* (2013.01); *G01N 27/3276* (2013.01); *G01N 33/5438* (2013.01); *G01N 33/56911* (2013.01); *G01N 33/56938* (2013.01); *A61B 2503/40* (2013.01); *A61B 2562/125* (2013.01); *Y02A 50/52* (2018.01); *Y02A 50/57* (2018.01)

(56) References Cited

U.S. PATENT DOCUMENTS

| | | | |
|---|---|---|---|
| 4,562,157 A | 12/1985 | Lowe et al. | |
| 4,704,353 A | 11/1987 | Humphries et al. | |
| 4,765,341 A * | 8/1988 | Mower | A61N 1/0587 |
| | | | 606/129 |
| 4,822,566 A | 4/1989 | Newman | |
| 4,847,193 A | 7/1989 | Richards et al. | |
| 4,883,057 A | 11/1989 | Broderick | |
| 4,927,502 A | 5/1990 | Reading et al. | |
| 5,063,081 A | 11/1991 | Cozzette et al. | |
| 5,140,393 A | 8/1992 | Hijikihigawa et al. | |
| 5,203,327 A | 4/1993 | Schoendorfer et al. | |
| 5,482,830 A | 1/1996 | Bogart et al. | |
| 5,492,840 A | 2/1996 | Malmqvist et al. | |
| 5,601,694 A | 2/1997 | Maley et al. | |
| 5,628,890 A * | 5/1997 | Carter | C12Q 1/001 |
| | | | 204/403.05 |
| 5,629,213 A | 5/1997 | Kornguth et al. | |
| 5,722,397 A | 3/1998 | Eppstein | |
| 5,834,224 A | 11/1998 | Ruger et al. | |
| 5,869,272 A | 2/1999 | Bogart et al. | |
| 6,013,029 A | 1/2000 | Korf et al. | |
| 6,096,497 A | 8/2000 | Bauer | |
| 6,107,080 A | 8/2000 | Lennox | |
| 6,210,551 B1 | 4/2001 | Osman et al. | |
| 6,267,722 B1 | 7/2001 | Anderson et al. | |
| 6,322,963 B1 | 11/2001 | Bauer | |
| 6,346,376 B1 | 2/2002 | Sigrist et al. | |
| 6,346,387 B1 | 2/2002 | Stewart et al. | |
| 6,375,829 B1 | 4/2002 | Shevchenko et al. | |
| 6,436,699 B1 | 8/2002 | Berggren et al. | |
| 6,503,701 B1 | 1/2003 | Bauer | |
| 6,544,729 B2 | 4/2003 | Sayler et al. | |
| 6,573,107 B1 | 6/2003 | Bowen et al. | |
| 6,585,663 B1 | 6/2003 | Coley et al. | |
| 6,602,400 B1 | 8/2003 | Choong et al. | |
| 6,650,919 B2 | 11/2003 | Edelberg et al. | |
| RE38,525 E | 6/2004 | Stanley et al. | |
| 6,751,491 B2 | 6/2004 | Lew et al. | |
| 6,770,190 B1 | 8/2004 | Milanovski et al. | |
| 6,787,368 B1 | 9/2004 | Wong et al. | |
| 6,821,529 B2 | 11/2004 | Nelson | |
| 6,846,654 B1 | 1/2005 | Blackburn et al. | |
| 6,914,279 B2 | 7/2005 | Lu et al. | |
| 6,942,771 B1 * | 9/2005 | Kayyem | B01L 3/5027 |
| | | | 204/409 |
| 6,967,074 B2 | 11/2005 | Duffy et al. | |
| 6,977,160 B2 | 12/2005 | Yanagawa et al. | |
| 7,052,854 B2 | 5/2006 | Melker et al. | |
| 7,125,660 B2 | 10/2006 | Stanton et al. | |
| 7,138,121 B2 | 11/2006 | Spangler et al. | |
| 7,163,788 B2 | 1/2007 | Tong | |
| 7,271,007 B2 | 9/2007 | Weigl et al. | |
| 7,291,496 B2 | 11/2007 | Holm-Kennedy | |
| 7,292,349 B2 | 11/2007 | Miller et al. | |
| 7,309,566 B2 | 12/2007 | Fulton et al. | |
| 7,309,614 B1 | 12/2007 | Baird et al. | |
| 7,317,216 B2 | 1/2008 | Holm-Kennedy | |
| 7,332,314 B2 | 2/2008 | Chang et al. | |
| 7,349,080 B2 | 3/2008 | Aklian | |
| 7,399,585 B2 | 7/2008 | Gau | |
| 7,455,756 B2 | 11/2008 | Choi et al. | |
| 7,473,551 B2 | 1/2009 | Warthoe | |
| 7,521,019 B2 | 4/2009 | Polak et al. | |
| 7,531,002 B2 | 5/2009 | Sutton et al. | |
| 7,632,633 B2 | 12/2009 | Iwai et al. | |
| 7,687,258 B1 | 3/2010 | Maki | |
| 7,766,862 B2 | 8/2010 | Gerber et al. | |
| 7,985,384 B2 | 7/2011 | Yazawa et al. | |
| 8,067,184 B2 | 11/2011 | Schwoebel et al. | |
| 8,106,428 B2 | 1/2012 | Koh et al. | |
| 8,153,445 B2 | 4/2012 | Chen et al. | |
| 8,158,342 B2 | 4/2012 | Chen et al. | |
| 8,216,797 B2 | 7/2012 | Schwoebel et al. | |
| 8,349,604 B2 | 1/2013 | Mohapatra et al. | |
| RE43,978 E | 2/2013 | Holm-Kennedy | |
| 8,374,796 B2 | 2/2013 | Fernandez | |
| 8,425,492 B2 | 4/2013 | Herbert et al. | |
| 8,442,611 B2 | 5/2013 | Santini, Jr. et al. | |
| 8,450,056 B2 | 5/2013 | Miller et al. | |
| 8,486,619 B2 | 7/2013 | Miller et al. | |
| 8,591,459 B2 | 11/2013 | Clymer et al. | |
| 8,623,196 B2 | 1/2014 | Kohli et al. | |
| 8,649,840 B2 | 2/2014 | Sheppard, Jr. et al. | |
| 8,673,626 B2 | 3/2014 | Chang et al. | |
| 8,834,946 B2 | 9/2014 | Abramson et al. | |
| 8,841,137 B2 | 9/2014 | DeLouise et al. | |
| 8,898,069 B2 | 11/2014 | Hood et al. | |
| 8,900,879 B2 | 12/2014 | Lin et al. | |
| 8,914,090 B2 | 12/2014 | Jain et al. | |
| 9,029,168 B2 | 5/2015 | McAlpine et al. | |
| 9,034,638 B2 | 5/2015 | Miller et al. | |
| 9,097,676 B2 | 8/2015 | Meinhart et al. | |
| 9,217,745 B2 | 12/2015 | Miller et al. | |
| 9,267,919 B1 | 2/2016 | Larkins et al. | |
| 2003/0009097 A1 * | 1/2003 | Sheraton | A61B 5/0408 |
| | | | 600/392 |
| 2004/0146899 A1 * | 7/2004 | Kayyem | B82Y 15/00 |
| | | | 435/6.11 |
| 2006/0155174 A1 * | 7/2006 | Glukhovsky | A61B 1/00036 |
| | | | 600/301 |
| 2007/0179568 A1 * | 8/2007 | Nycz | A61B 5/0031 |
| | | | 607/60 |
| 2008/0200343 A1 * | 8/2008 | Clemens | B01L 3/502715 |
| | | | 506/9 |
| 2008/0204043 A1 * | 8/2008 | Wang | B82Y 15/00 |
| | | | 324/633 |
| 2009/0084686 A1 | 4/2009 | Yun et al. | |
| 2009/0143659 A1 | 6/2009 | Li et al. | |
| 2009/0184002 A1 | 7/2009 | Furukawa et al. | |
| 2010/0116682 A1 * | 5/2010 | Neuzil | G01N 27/403 |
| | | | 205/419 |
| 2010/0298679 A1 | 11/2010 | Wu et al. | |
| 2010/0331771 A1 * | 12/2010 | Mazza | A61B 5/150633 |
| | | | 604/66 |
| 2011/0115499 A1 * | 5/2011 | Chodavarapu | G01R 27/26 |
| | | | 324/649 |
| 2011/0189705 A1 * | 8/2011 | Gao | G01N 33/54306 |
| | | | 435/7.92 |
| 2011/0275912 A1 | 11/2011 | Boyden et al. | |
| 2012/0088315 A1 | 4/2012 | Merelle et al. | |
| 2012/0135509 A1 * | 5/2012 | Hall | C12Q 1/001 |
| | | | 435/287.1 |
| 2012/0209090 A1 * | 8/2012 | Goodall | A61B 5/0071 |
| | | | 600/309 |

(56) References Cited

U.S. PATENT DOCUMENTS

2013/0053665 A1    2/2013  Hughes et al.
2013/0213823 A1*   8/2013  Arumugam ........ G01N 27/3278
                                                        205/794.5

OTHER PUBLICATIONS

Geng et al., "Self-assembled monolayers-based immunosensor for detection of *Escherichia coli* using electrochemical impedance spectroscopy", Electrochimica Acta 53, 2008, pp. 4663-4668.
Wang et al., "New Trends in Impedimetric Biosensors for the Detection of Foodborne Pathogenic Bacteria", Sensors, 2012, vol. 12, pp. 3449-3471.
Wisniewski et al., "Methods for reducing biosensor membrane biofouling", Colloids and Surfaces B: Biointerfaces, 2000, vol. 18, pp. 197-219.
Zheng, "The development of an aptamer-based surface plasmon resonance (SPR) sensor of the real-time detection of glycated protein", The University of Toledo, Theses and Dissertation, 2012, pp. 1-206.
European Examination Report, Application No. EP14779197.4 dated Oct. 20, 2017.
Second Chinese Office Action, Application No. 201480026380.4, dated Jun. 13, 2017.
PCT International Search Report and the Written Opinion, Application No. PCT/US2014/023126 filed Mar. 11, 2014, dated Jul. 9, 2014.
Intellectual Property India, Examination report under sections 12 & 13 of the Patents Act, 1970 and the Patents Rules, 2003, Application No. 6073/CHENP/2015, dated Mar. 3, 2020.

* cited by examiner

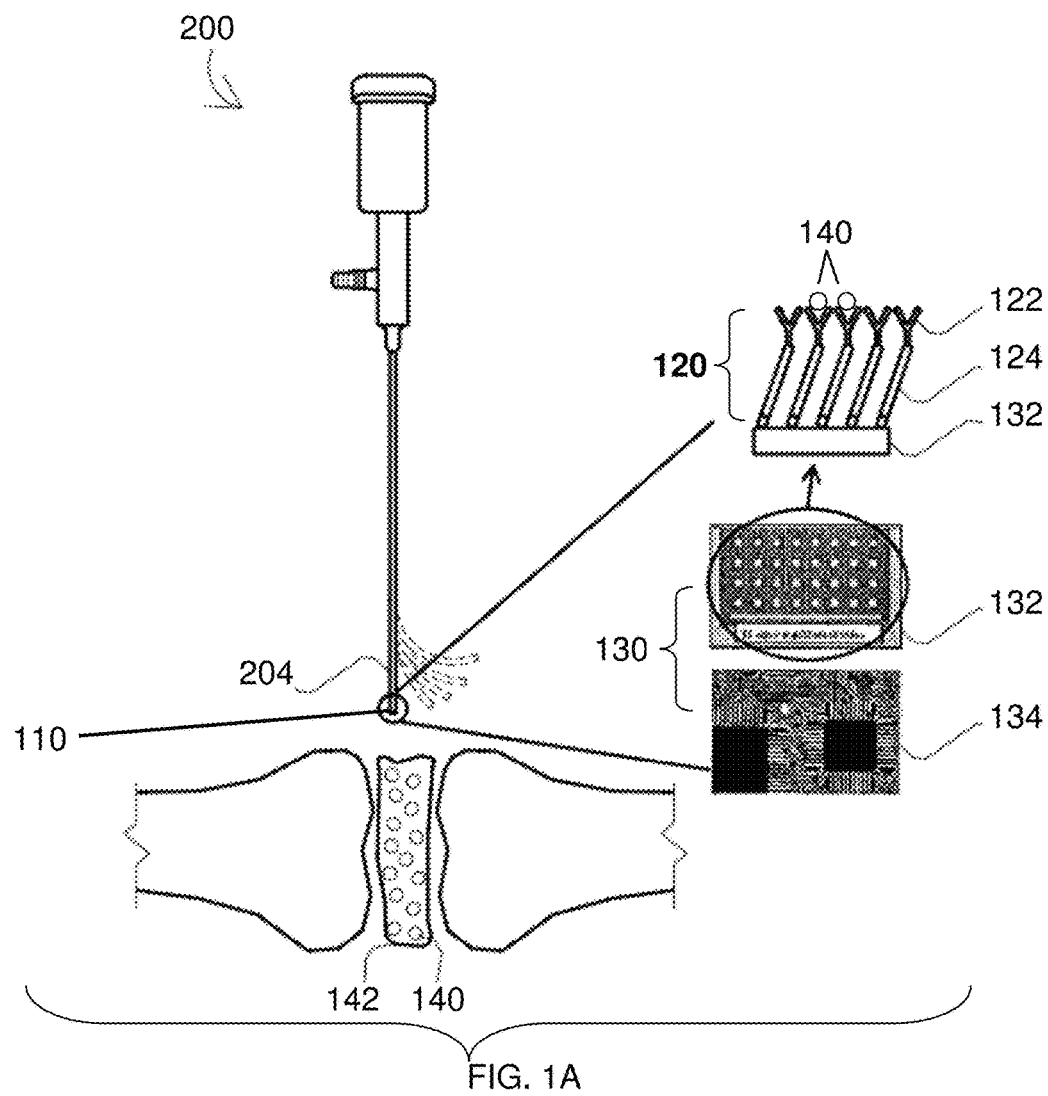
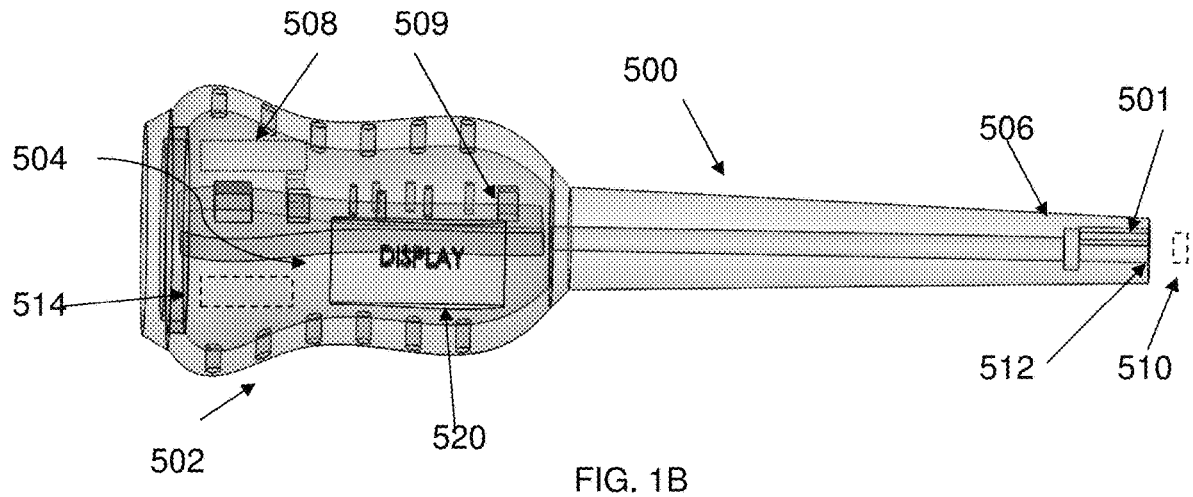
FIG. 1A
FIG. 1B

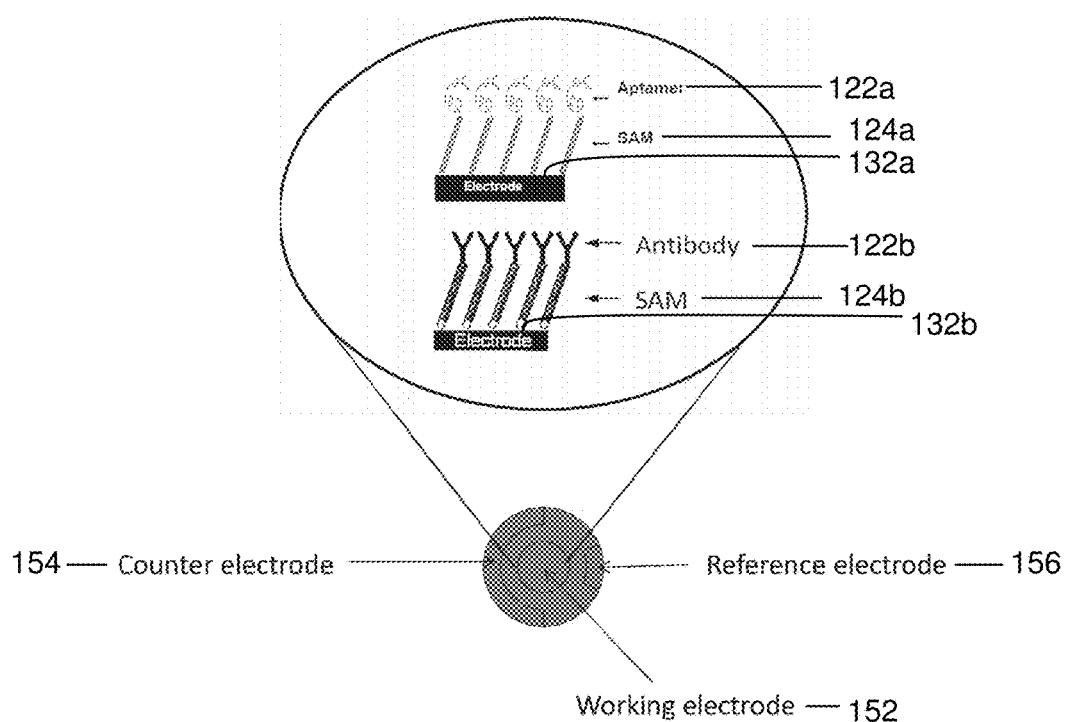
FIG. 2
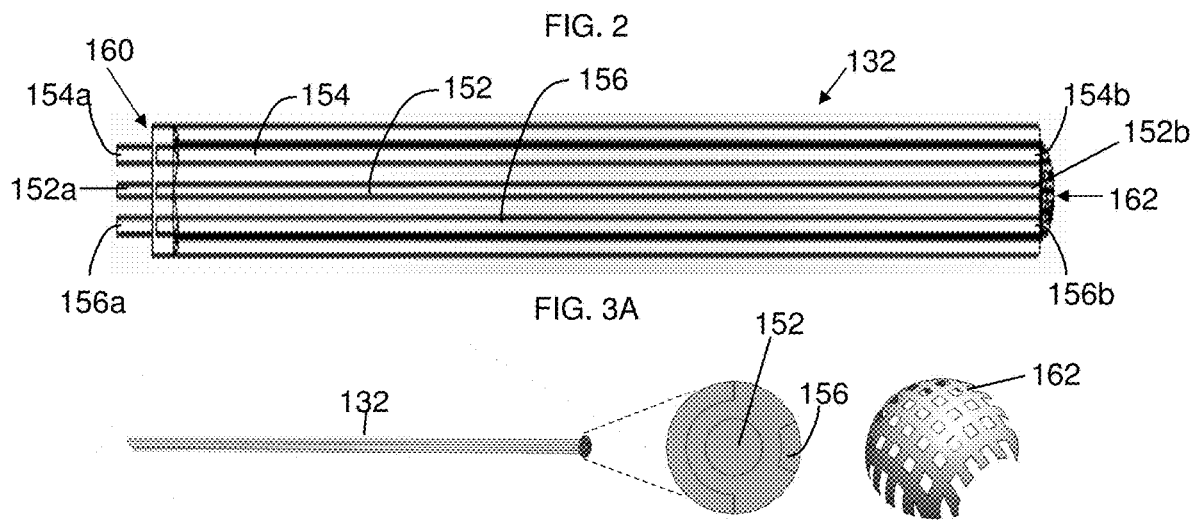
FIG. 3A
FIG. 3B  FIG. 3C

BIOSENSOR DEVICE TO TARGET ANALYTES IN SITU, IN VIVO, AND/OR IN REAL TIME, AND METHODS OF MAKING AND USING THE SAME

RELATED APPLICATIONS

This application is a national stage application filed under 35 U.S.C. § 371 of international application PCT/US14/23126, filed under the authority of the Patent Cooperation Treaty on Mar. 11, 2014, published; which claims priority to U.S. provisional patent application 61/775,939, filed under 35 U.S.C. § 111(b) on Mar. 11, 2013. The entire disclosures of all the aforementioned applications are expressly incorporated herein by reference for all purposes.

STATEMENT REGARDING FEDERALLY SPONSORED RESEARCH

This invention was not made with any government support, and the government has no rights in the invention.

TECHNICAL FIELD

The present disclosure pertains to the field of sensing target analytes in real time and in situ.

BACKGROUND OF THE INVENTION

It is difficult to detect the presence of a target analyte directly either in a sample (e.g., in situ) or inside a body (e.g., in vivo). Currently, target analytes are detected by removing a sample and submitting such sample to a laboratory for analysis. It is also difficult to detect the target analyte in real time. Current techniques require a sample to be taken from a patient and then analyzed in a laboratory which greatly delays the timing of any diagnosis or detection of possibly toxic analytes. There is a need for a sensor with improved sensing characteristics and real-time in vivo/in situ detection capability. It would be further beneficial to have a sensor capable of rapid differentiation between viral and bacterial infections, and, if bacterial, segmentation into either Gram-positive or Gram-negative bacteria.

SUMMARY OF THE INVENTION

Disclosed herein is a biosensor for detecting the presence of a target analyte.

In a first aspect, a biosensor includes: a transducer component comprising an electrode operatively connected to a microprocessor, the microprocessor being adapted to receive, process and transmit a signal; and, a receptor component having: i) a sensing element capable of detecting and binding to at least one target analyte present in a sample; and, ii) a self-assembled monolayer (SAM), the SAM being positioned between and in contact with the sensing element and the electrode. The transducer component and the receptor component are capable of being brought into direct contact with the sample in situ. In use, the sensing element, in the presence of target analyte present in the sample, causes a detectable signal capable of being transmitted to the electrode via the SAM.

In certain embodiments, the presence of the target analyte is detected in real time.

In certain embodiments, the sensing element comprises at least one antibody capable of detecting at least one bacterial target analyte.

In certain embodiments, the sample comprises a fluid or tissue in a living organism. In certain embodiments, the sample comprises a fluid or tissue in a living organism in vivo. In certain embodiments, the sample comprises a fluid or tissue in a living animal. In certain embodiments, wherein the sample comprises a fluid or tissue in a human.

In certain embodiments, the sample comprises a food product.

In certain embodiments, the rate and degree of signal change correspond to the presence and concentration of the target analyte.

In certain embodiments, the presence of the target analyte is detected by impedance signal. In certain embodiments, the detectable signal comprises a change in impedance as a function of frequency.

In certain embodiments, the presence of the target analyte is detected by amperometric or potentiometric signal.

In certain embodiments, the electrode comprises a micro-interdigitated gold electrode.

In certain embodiments, the detectable signal is displayed on the microprocessor through radio frequency identification (RFID).

In certain embodiments, the biosensor is integrated into a medical, dental, or veterinary device having a tissue-contacting surface.

In certain embodiments, the target analyte comprises *Staphylococcus aureus*. In certain embodiments, the target analyte comprises methicillin-resistant *Staphylococcus aureus* (MRSA).

In certain embodiments, the target analyte comprises *Streptococcus pyogenes, Streptococcus pneumoniae*, or *Streptococcus agalactiae*.

In certain embodiments, the target analyte comprises a virus, or portion thereof.

In certain embodiments, the target analyte comprises a molecule, or portion thereof, that is a marker for a cancer.

In certain embodiments, the SAM comprises mercaptoproprionic acid (MPA), 11-mercaptoundecanoic acid (MUA), 1-tetradecanethiol (TDT), or dithiobios-N-succinimidyl propionate (DTSP).

In another aspect, there is provided herein a kit comprising the biosensor device described herein.

In another aspect, there is provided herein a method of making a biosensor capable of detecting a target analyte in situ in a sample. The method generally includes linking a sensing element to an electrode via a self-assembled monolayer (SAM); and operatively connecting a microprocessor to the electrode such that, when the sensing element binds to a target analyte present in situ in a sample, the microprocessor detects and transmits a signal.

In another aspect, there is provided herein a method of detecting a bacterial infection in a living organism, which includes placing the biosensor device described herein at least partially in or on the living organism sufficient to come into contact with any bacterial target analyte present in the living organism; and, detecting the presence of the bacterial target analyte when the biosensor device transmits the detectable signal.

In certain embodiments, the biosensor device determines whether the bacterial target analyte is Gram-positive or Gram-negative, and the biosensor device transmits a signal to the medical instrument indicating whether the bacterial target analyte is Gram-positive or Gram-negative.

In certain embodiments, the change in the physical properties of the sensing matrix that is detected comprises the change in impedance as a function of frequency.

The biosensor may be adapted and incorporated into any of several suitable medical instruments or surgical tools, including on the flexible tip of an elongated medical instrument. In certain embodiments, the sensing element comprises antibodies, and the sensor is adapted to detect the presence of a bacteria.

Further provided herein is a method of detecting the presence and/or determining the amount of bacteria present in a body.

BRIEF DESCRIPTION OF THE DRAWINGS

FIG. 1A is a schematic representation of a biosensor device operatively connected at a distal end of a flexible tip of a medical instrument.

FIG. 1B is a schematic representation of another embodiment of an instrument that either incorporates a biosensor device and/or can be configured to have a biosensor device operatively attached to the instrument.

FIG. 2 is a schematic representation of a portion of a biosensor device.

FIG. 3A is a schematic side elevational representation of an embodiment of an electrode useful in a biosensor device.

FIG. 3B is a cross-sectional schematic representation of an electrode having a working electrode, a counter electrode, and a reference electrode.

FIG. 3C is perspective view of a protective membrane useful with the electrode shown in FIG. 3B.

DETAILED DESCRIPTION OF THE INVENTION

Definitions

Figure 4:
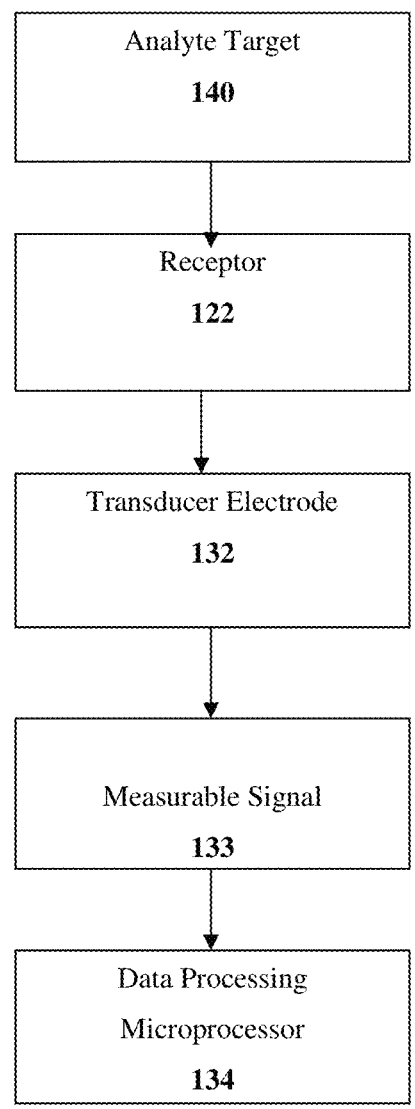
FIG. 4 is a schematic representation of a method for detecting a target analyte.

It is to be understood that both the foregoing general description and the following detailed description are exemplary and explanatory only and are not intended to limit the scope of the current teachings. In this application, the use of the singular includes the plural unless specifically stated otherwise.

The use of the word "a" or "an" when used in conjunction with the term "comprising" in the claims and/or the specification may mean "one," but it is also consistent with the meaning of "one or more," "at least one," and "one or more than one."

Also, the use of "comprise", "contain", and "include", or modifications of those root words, for example but not limited to, "comprises", "contained", and "including", are not intended to be limiting. The term "and/or" means that the terms before and after can be taken together or separately. For illustration purposes, but not as a limitation, "X and/or Y" can mean "X" or "Y" or "X and Y".

Throughout the entire specification, including the claims, the word "comprise" and variations of the word, such as "comprising" and "comprises" as well as "have," "having," "includes," and "including," and variations thereof, means that the named steps, elements, or materials to which it refers are essential, but other steps, elements, or materials may be added and still form a construct within the scope of the claim or disclosure. When recited in describing the invention and in a claim, it means that the invention and what is claimed is considered to be what follows and potentially more. These terms, particularly when applied to claims, are inclusive or open-ended and do not exclude additional, unrecited elements or method steps.

Various embodiments are described herein in the context of apparatus, method, system, and/or process for sensing target analytes, such as bacteria or viruses or portions thereof. Those of ordinary skill in the art will realize that the following detailed description of the embodiments is illustrative only and not intended to be in any way limiting. Other embodiments will readily suggest themselves to such skilled persons having the benefit of this disclosure. Reference to an "embodiment," "aspect," or "example" herein indicate that the embodiments of the invention so described may include a particular feature, structure, or characteristic, but not every embodiment necessarily includes the particular feature, structure, or characteristic. Further, repeated use of the phrase "in one embodiment" does not necessarily refer to the same embodiment, although it may.

In the interest of clarity, not all of the routine features of the implementations or processes described herein are shown and described. It will be appreciated that numerous implementation-specific adaptations are incorporated to achieve specific goals, such as compliance with application- and business-related constraints, and that these specific goals vary from one implementation to another and from one developer to another. Moreover, it will be appreciated that such a development effort might be complex and time-consuming, but would nevertheless be a routine undertaking for those of ordinary skill in the art having the benefit of this disclosure.

Described herein is a biosensor device for detecting the presence and/or determining the amount of a target analyte in situ and in real time.

Referring first to a schematic representation of one embodiment of a biosensor device shown in FIGS. 1-3, a biosensor device 110 includes a receptor component 120 and a transducer component 130. The transducer component 130 is responsive to changes that occur in the receptor component 120 from the interaction between a sensing element and a target analyte for generating measurable signals, as further explained herein.

Referring now to FIG. 1A, an example of a biosensor 110 that is operatively connected to an instrument 200 is shown. For ease of explanation, the biosensor device 110 is shown as being positioned on a contact member 204 such as a distal end of a flexible tip of the instrument 200. It is to be understood, however, that other embodiments are within the contemplated scope of the disclosure herein.

The transducer component 130 is comprised of at least one electrode 132, and at least one microprocessor 134. The microprocessor 134 is adapted to transmit and process a signal, as further explained herein. It is to be understood that the microprocessor 134 can include the generating an electronic image for review by a skilled person.

In certain embodiments, the biosensor device 110 can include more than one transducer component 130. In such embodiments, each electrode 132 is operatively connected to a corresponding microprocessor 134.

The receptor component includes one sensing (or receptor) element, 122 and a self-assembled monolayer (SAM) 124. The sensing element 122 is capable of detecting and binding to at least one target analyte 140. The self-assembled monolayer (SAM) 124 is positioned between and is in contact with both the sensing element 122 and the electrode 132. The sensing element 122, in the presence of the target analyte 140, causes a detectable signal capable of being transmitted to the electrode 132.

When the sensing element 122 contacts a sample 142 (for example, a fluid or tissue), and binds to the target analyte 140 that is present in the sample 142, a change in at least one physical property is detected by the electrode 132, and is transmitted as a signal by the microprocessor 134. As further described herein, in certain embodiments, the change in the physical property that is detected comprises the change in impedance as a function of frequency.

FIG. 1B is a schematic representation of another embodiment of an instrument 500 that either incorporates a biosensor device 501 and/or can be configured to have a biosensor device 510 operatively attached to the instrument 500. The instrument 500 generally includes a proximal handle end 502 that defines an annular opening 504, and a distal probe end 506 that is configured to hold either the integral biosensor 501 or the attachable biosensor device 510. It is to be understood that the biosensor devices 501/510 can generally include a transducer component (e.g., electrode and microprocessor) and a receptor component (e.g., SAM and sensing element) that are similarly configured as described elsewhere herein. It is also to be understood that such electrode is positioned to come into contact with a power source 508, such as a battery, and a microprocessor 508. The biosensor 501/510 can be attached to the distal probe end 506 of the handle 502 in a suitable manner. For example, the distal probe end 506 can define one or more detents 512 so that the biosensor 501 can be snapped onto the distal probe end 506. In another embodiment, the biosensor 501 can be screwed or threaded onto the distal probe end 506. In certain embodiments the biosensor device 501/510 can be either removably attached, or permanently attached, to the distal probe end 506.

In certain embodiments, at least one of the entire instrument 500, the biosensor device 501/510, the handle end 502, and/or the distal probe end 506 can be disposable and/or configured to be attached and used in a sterile condition.

In certain embodiments, the annular opening 504 can also be configured to contain an RFID 514 for transmitting the detected signal. In addition, the instrument 500 can include a display 520 that is operatively connected to the microprocessor 508. The display 520 can be configured to display different types of information; for example, "+" or "−", type of target analyte present, quantitative amount of analyte present, and the like.

In certain embodiments, as schematically illustrated in FIG. 2, multiple target analytes can be sensed simultaneously. For example, the biosensor device 110 can include an electrode having a first side 110a on which a first SAM layer 124a is affixed, and a second side of the electrode 101b on which a second SAM layer 124b is affixed.

FIGS. 3A-3C show one embodiment of an electrode 132 suitable for use in the biosensor device 110. The electrode 132 can include a working electrode component 152, a counter electrode component 154, and a reference electrode 156. In the embodiment show, the working electrode component 152, the counter electrode component 154, and the reference electrode 156 each have proximal ends, 152a, 154a, and 156b, respectively that are integrated on a first end 160 of the electrode 132. The first end 160 can be configured to be connected to a socket of an impedance analyzer. In certain embodiments, one or more of distal ends, 152b, 154b and 156b, respectively, of the working electrode component 152, the counter electrode component 154, and the reference electrode component 156 can be protected by a suitable membrane 162. In the embodiments shown in FIG. 3C, the membrane 162 can be comprised of an electrode mesh.

Referring back to FIG. 2, there is shown a pathogen-specific aptamer 122a linked to the first side 110a of the working electrode 132 via a first SAM layer 124a. Also shown is a pathogen-specific antibody 124b linked to a second side 110b (or, as alternately shown as a second electrode 110b) of the working electrode 152 via a second SAM layer 124b.

In certain embodiments, the three electrode system (working 152, counter 154 and reference 156 electrodes) are useful for the electrochemistry analysis of a reaction causing electrical current flow. The binding reaction occurs on the working electrode 152. The counter electrode 154 and the reference electrode 156 generate electrical potentials against other potentials to be measured.

It is to be understood that the biosensor device can be configured to compensate for any noise at the time of the sampling where post-processing can include an algorithm that is applied through a software program to remove random noise, slopes, and the like.

It is also to be understood that the following can be determined experimentally by characterizing one or more of, for example: electrode size, drive voltage, environmental conditions such as temperature, analyte binding concentration, and the like.

The biosensor device can be configured to be adapted for use on small (e.g., nanoscale) samples. Also, the receptor component 120 can be configured to have different sensing elements 122 that can be clustered or arrayed for use in detection of multiple target analytes 140.

FIG. 4 depicts an example process flow diagram for using the biosensor device 110. When an analyte target 140 is present, there is a binding between the target 1 analyte 140 and a target-specific receptor 122, which is, in turn, bound to the electrode 132. The electrode 132 detects a signal 133 (e.g., alteration in impedance, etc.) and a measurable signal 133 is generated. The measurable signal 133 is processed by the microprocessor 134, thereby detecting the presence or absence of the target analyte 140.

Receptors

Non-limiting examples of "receptor" can include an antibody, an antibody fragment, an aptamer, or an enzyme, or portions thereof.

The term "antibody" or "antibodies" as used herein refers to proteins used by the immune system to identify and/or neutralize foreign targets such as bacteria or viruses. Antibodies tend to be Y-shaped glycoproteins produced by B-cells and secreted by plasma cells. Antibodies recognize particular parts of a target known as antigens and bind to a specific epitope thereon. "Antibody" can be used interchangeably with "immunoglobulin" and is meant to include all known isotypes and natural antibodies.

In certain embodiments, the sensing element comprises antibodies specific for a target analyte to be sensed, such as *Staphylococcus aureus* antibodies in a sensor designed to detect the presence of *Staphylococcus aureus*. The antibodies can be synthesized or bought commercially.

In certain embodiments, the biosensor device can calibrated to both detect and quantify an amount of a target analyte present.

Electrodes

As used herein, "electrode" generally includes a composition, which, when connected to an electronic device, is able to sense a current or charge and convert it to a signal. Alternatively, an electrode can be a composition which can apply a potential to and/or pass electrons to or from connected devices.

Different electrodes include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). In one embodiment, the electrode can be a micro interdigitated gold electrode (MIGE).

Self-Assembled Monolayers (SAM) Layers

In the embodiments herein, the SAM layer 124 generally comprises a surface deposit on a surface of the electrode 132. Depending on the target analyte 140 to be detected, the SAM layer 140 that can substantially cover, or can partially cover, an area on the surface of the electrode 132. The SAM layer 124 generally comprises one or more organic molecules such that the SAM molecules act as a linker between the sensing element 122 and the electrode 132.

As one non-limiting example, a SAM is formed with mercaptoproprionic acid (MPA), which is readily bound with the amino group in certain antibodies via covalent bonding. In other non-limiting embodiments, a SAM is made from 11-mercaptoundecanoic acid (MUA), 1-tetradecanethiol (TDT), or dithiobios-N-succinimidyl propionate (DTSP). One suitable method of making and characterizing a monolayer is described in chapter 6 of *Electrochemistry—A Laboratory Textbook; A workbook for the* 910 *PSTAT mini*, Barbara Zumbrägel, Metrohm Monograph, January, 2013, the disclosure of which is hereby incorporated by reference.

Detectable Signals

In one embodiment, biosensor device detects electrochemical signals that may comprise, for example, conductivity signals, capacitance signals, impedance signals, potentiometric signals, or voltammetric signals. In embodiments comprising potentiometric sensors, a potential signal developed at the electrode/electrolyte surface is used to quantify the concentration of analyte present. In embodiments comprising voltammetric or amperometric sensors, a constant voltage signal is applied to the system and corresponding electrical current is used to quantify the analyte. Variable (linear or cyclic) voltage can be applied and the height of the peak in the current—voltage curve is used to quantify the analyte.

Figure 5:
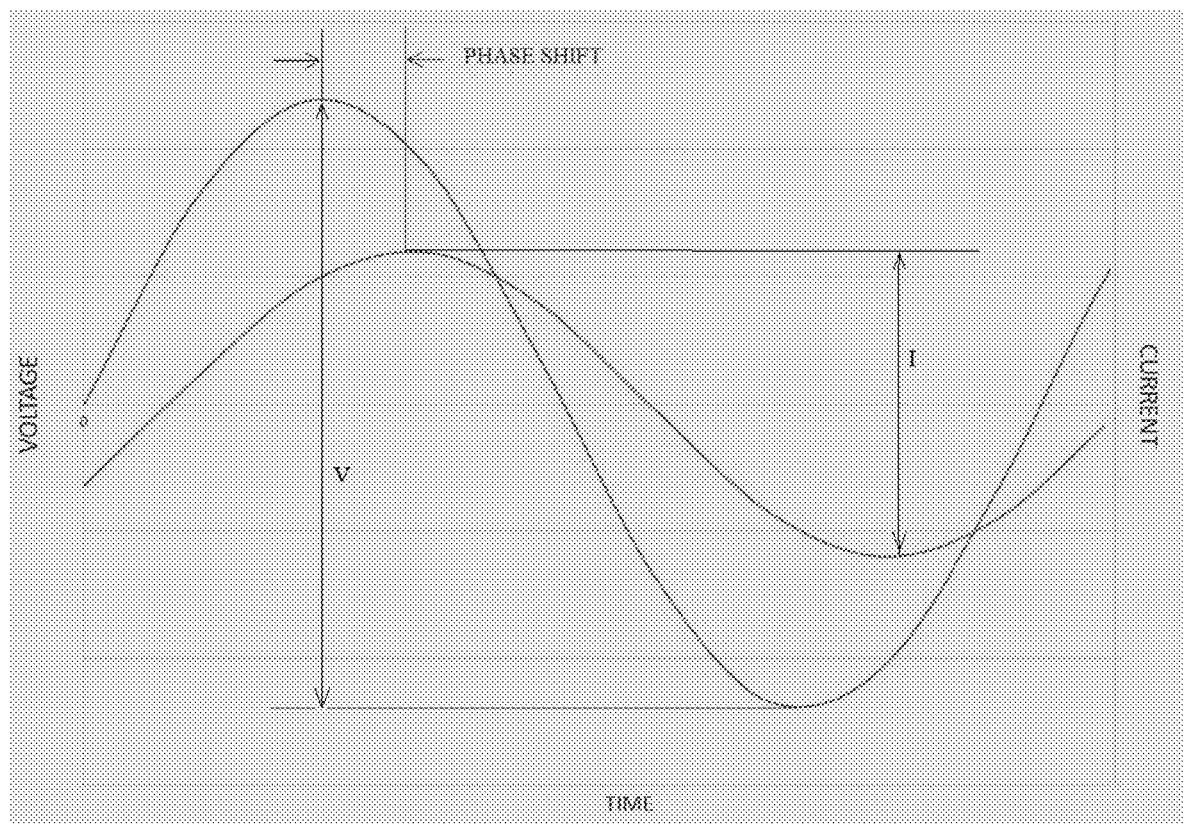
FIG. 5 is a graph depicting a shifted sine wave current response to an applied sine wave voltage.

In some embodiments, the biosensor device utilizes electrochemical impedance spectroscopy, which measures impedance over a range of frequencies, to quantify the analyte. When a sine wave voltage is applied to a system, it produces a shifted sine wave current response. The impedance (Z) has two components: magnitude and phase shift (angle). This is illustrated in FIG. 5. The rate and degree of impedance change represent the presence and concentration of bacteria. Impedance can be calculated according to the equations:

$$|Z| = \frac{V}{I}$$

$$\varnothing = \text{Phase shift}$$

$$Z = |Z|e^{i\varnothing} \text{(polar coordinates)}$$

$$Z = Z_{real} + iZ_{img} \text{(cartesian coordinates)}$$

The microprocessor processes the signals and eventually displays the information. Signal processing can generally include a series of microelectronic channels that screen the sensor signals and control the noise, calibration, and amplification.

Figure 6A:
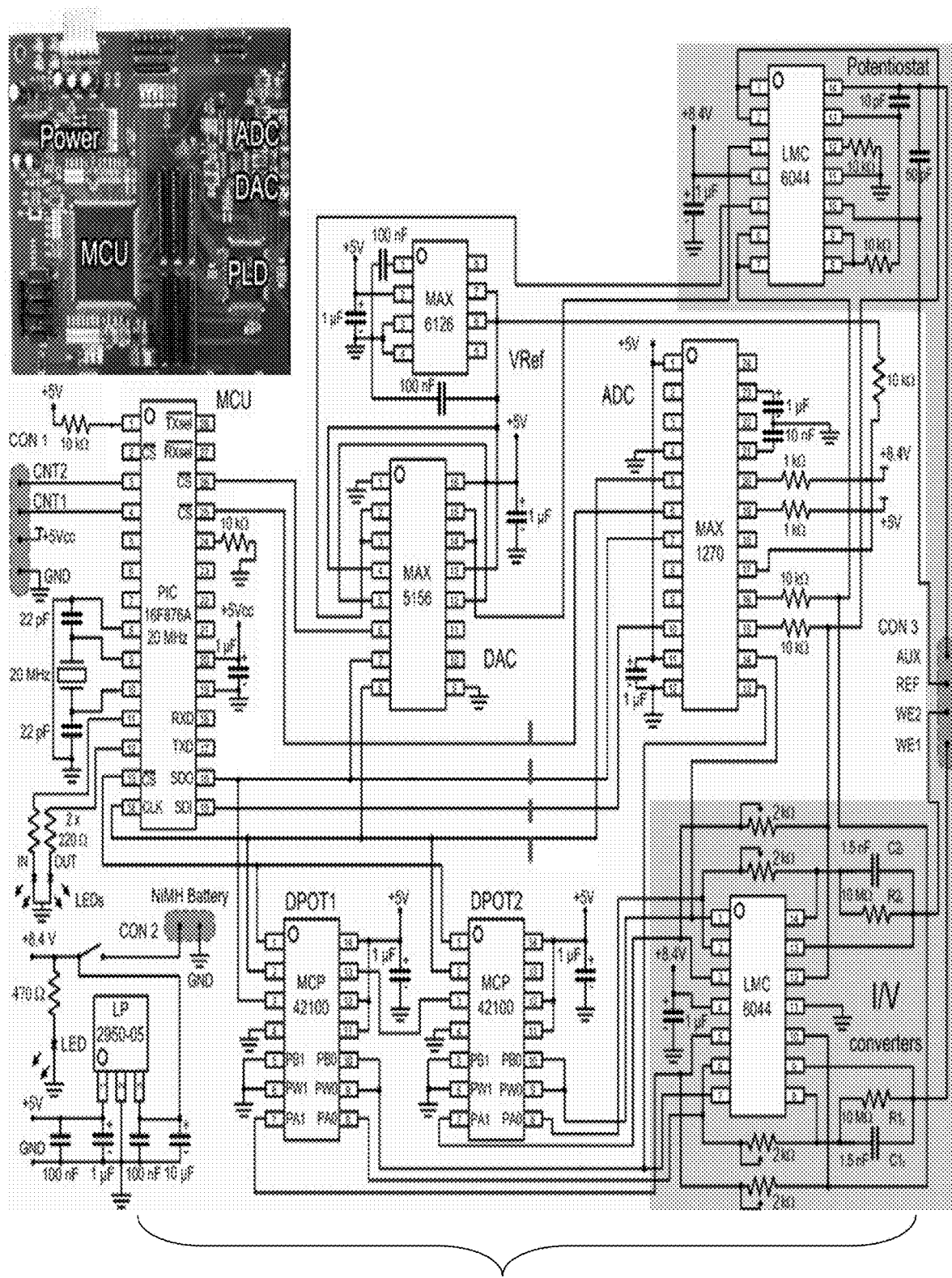
FIG. 6A is a schematic diagram of a circuit design for an electronic control system for use with the biosensor device illustrated in FIG. 1.
Figure 6B:
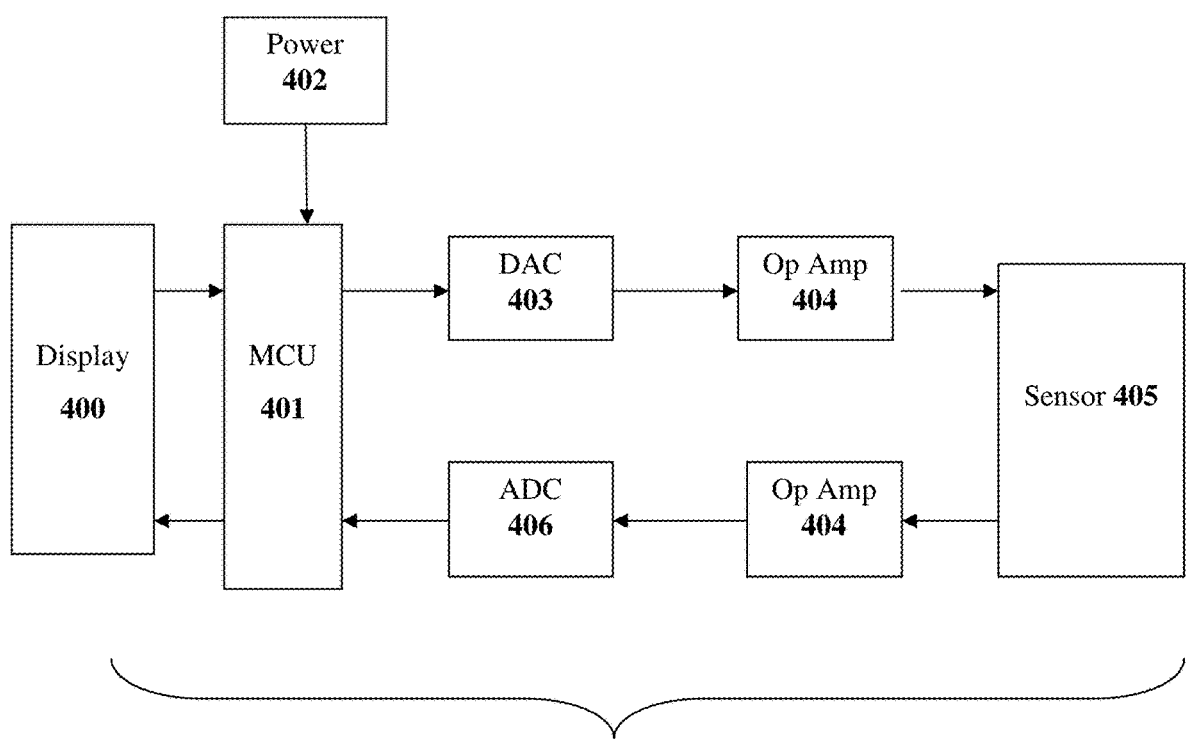
FIG. 6B is a box diagram of an electronic control system for use with the biosensor illustrated in FIG. 1 and FIG. 6A.
Figure 7:
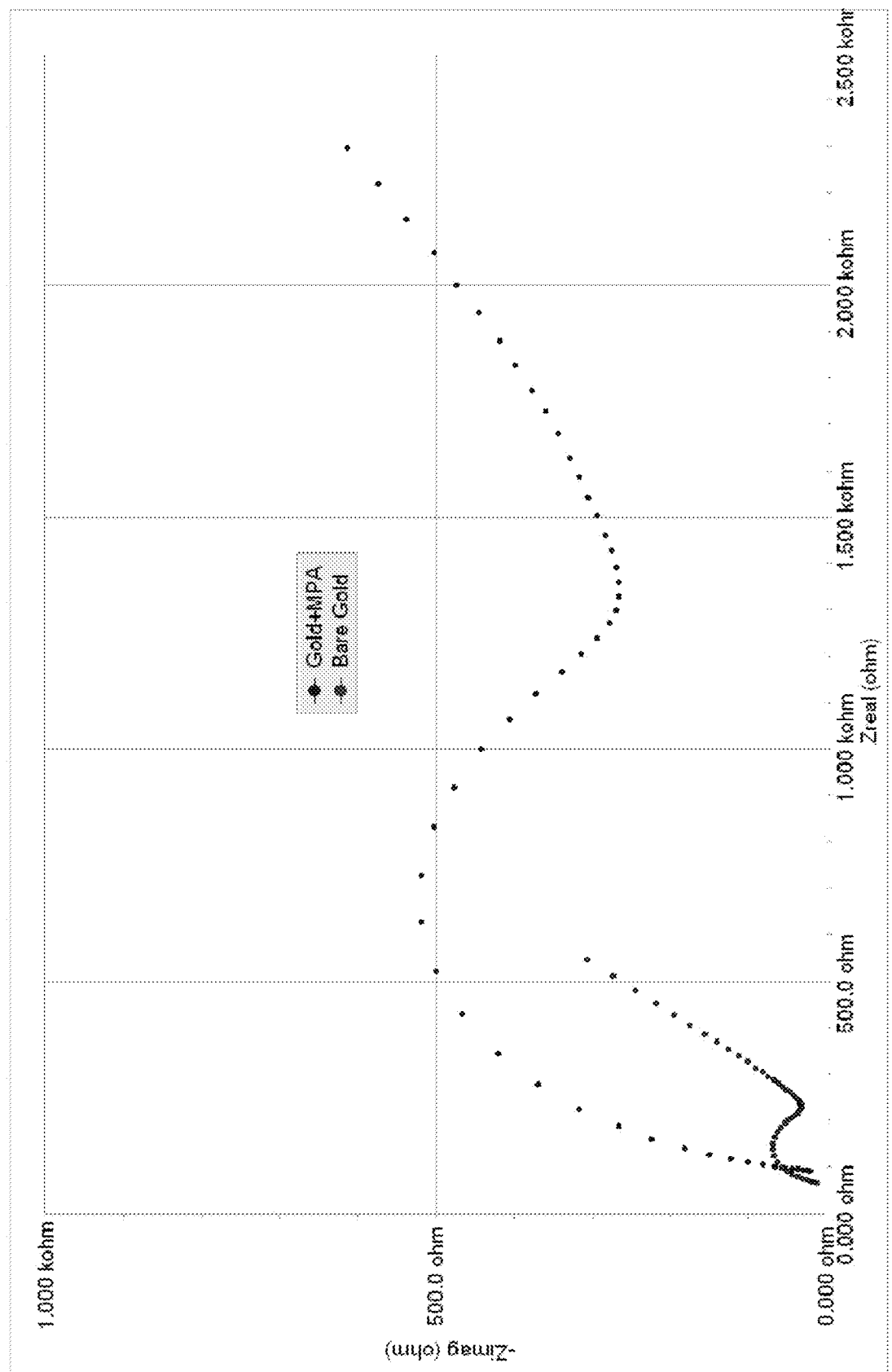
FIG. 7 is an impedance curve showing an impedance shift when the surface of a bare gold electrode is modified by SAM deposit.

FIG. 6A is a schematic diagram of an exemplary electronic control system for use with the biosensor described herein. FIG. 6B is an exemplary flow diagram where an analog signal is generated in the form of a current, which is then amplified by an operational amplifier (Op Amp) 404 to reduce noises in the voltage applied to the electrode and the measured current signal, to switch current and voltage, and to control amplification. The amplified signal is then converted to a digital signal by an analog-to-digital converter (ADC) 406. The digital signal is controlled and processed by a micro-controller unit (MCU) 401, having a power supply 402, to produce a display 400. The micro-controller unit 401 can utilize specialized software programs to perform various functions. The controlled signal is processed through a digital-to-analog converter (DAC) 403 and converted to an analog signal. Conversion to an analog signal gives potential to the sensor 405; the analog signal becomes an additional potential to the electrode. In some embodiments, radio frequency identification (RFID) can be utilized to directly display the sensing information on a computer.

In certain embodiments, the microprocessor program is composed to screen noise and to pick up impedance change at a very low frequency range; for example, from about 1 Hz to about 10 Hz.

The microprocessor includes an algorithm program capable of screening background noise and detecting up impedance signal that represent the presence and concentration of target analyte. The microprocessor program is composed to screen noise and to pick up impedance change at a very low frequency range. Also, in certain embodiments, the detectable signal can be displayed on the microprocessor through radio frequency identification (RFID).

Target Analytes

The term "target analyte" generally refers to any molecule that is detectable with a biosensor as described herein. Non-limiting examples of targets that are detectable in the biosensors described herein include, but are not limited to, biomolecules such as bacteria, viruses, proteins, nucleic acids, microRNAs, carbohydrates, and other types of small molecules such as microRNAs, and other such molecules that may indicate the presence of an infection, a cancer, or toxic analyte.

It is to be understood that the target analytes that can be detected using the biosensor device described herein can be present in a sample that comprises tissue or fluid of a living organism. Non-limiting examples of tissue include soft tissue, hard tissue, skin, surface tissue, outer tissue, internal tissue, a membrane, fetal tissue and endothelial tissue.

The living organism can be a mammal and can include pet animals, such as dogs and cats; farm animals, such as cows, horses and sheep; laboratory animals, such as rats, mice and rabbits; poultry, such as chicken and turkeys; and, primates, such as monkeys and humans. In one embodiment, the mammal is human. It is also to be understood that the sample can comprise, for example, a surgical incision, an open wound, a closed wound, an organ, skin, skin lesions, membranes, in situ fluids such as blood, urine, and the like.

In other embodiments, the sample can be a food source that could be contaminated by toxic organisms. Non-limiting examples of food sources can be grains, beverages, milk and dairy products, fish, shellfish, eggs, commercially prepared and/or perishable foods for animal or human consumption (e.g., ground meat, salads, and the like).

The sample can also be food tissue such as a fruit, an edible plant, a vegetable, a leafy vegetable, a plant root, a soy product, dead animal tissue, meat, fish and eggs, where the presence of the target analyte is indicative spoilage.

In other embodiments, the sample can be in an external environment, such a soil, water ways, sludge, commercial effluent, and the like.

In some embodiments designed to detect bacteria, the presence of bacteria is detected as the bacterial antigens are bound to the antibodies. As a result of this interaction, the electrochemistry on the electrode changes. The rate and degree of change in the signal can be detected through one of several different methods. In one embodiment, where amperometric sensing is conducted, the current change due to the bacteria-antibody interaction is transmitted through the electrode. In another embodiment, where impedance sensing is conducted, wherein the impedance variation in the electrode is measured.

The biosensor device may be designed to detect any specific bacteria that may cause infection in bone structure by incorporating antibodies specific to the bacteria into the sensing matrix. Though certain embodiments described herein comprise antibodies specific for *Staphylococcus aureus*, the biosensor device can be also designed to detect any Gram-positive or Gram-negative bacteria, and rapidly differentiate between the two.

By way of non-limiting example, antibodies specific for bacteria such as methicillin-resistant *Staphyloccus aureus* (MRSA), *Staphylococcus epidermis*, *Staphylococcus saprophyticus*, *Streptococcus pyogenes*, *Streptococcus pneumoniae*, *Streptococcus agalactiae*, *Escherichia coli*, *Legionella pneumophila*, *Pseudomonas aeruginosa*, *Enterococcus faecalis*, *E. Coli*, *Listeria*, *Cyclospora*, *Salmonella enteritidis*, *Helicobacter pylori*, *Tubercle bacillus* (TB), other *Bacillus*, *Clostridium botulinum*, *Clostridium difficile*, *Clostridium perfringens*, *Clostridium tetani*, *Sporohalobacter*, *Anaerobacter*, *Heliobacterium*, *Brucella abortus*, *Brucella canis*, *Brucella melitensis*, *Brucella suis*, *Cyanobacteria*, green sulfur bacteria, *Chloroflexi*, purple bacteria, *thermodesulfobacteria*, *hydrogenophilaceae*, *nitrospirae*, *Burkholderia cenocepacia*, *Mycobacterium avium*, *Mycobacterium leprae*, *Mycobacterium tuberculosis*, *Mycobacterium ulcerans*, *Lactobacillus*, *Lactococcus*, *Bordetella pertussis*, *Chlamydia pneumoniae*, *Chlamydia tracomatis*, *Chlamydia psittaci*, *Borrelia burgdorferi*, *Campylobacter jejuni*, *Francisella tularensis*, *Leptospira monocytogenes*, *Leptospira interrogans*, *Mycoplasma pneumoniae*, *Rickettsia rickettsii*, *Shigella sonnei*, *Traponema pallidum*, *Vibrio cholerae*, *Haemophilus influenzae*, *Neiserria meningitidis*, or *Yersinia pestis* can be incorporated into the sensing matrix, thereby enabling the biosensor to detect and/or quantify any such bacteria.

The biosensor device, as described herein, has applications in human treatment, veterinary care of animals, sampling of food source, determination of the presence of pathogens in an external environment, and the like. There is a need for rapid, accurate, and affordable methods to detect the presence of pathogens. In some embodiments, the biosensor device directly detects a pathogen. In other embodiments the biosensor device detects the antibodies, or immune response, to a pathogen.

Some examples of serious pathological agents in felines include, but are not limited to, *Bartonella henselae*, *Borrelia burgdorferi*, *Chlamydia psittaci*, *Dirofilaria immitis*, *Ehrlichia canis*, Feline Calicivirus, Feline Coronavirus, Feline Herpesvirus, Feline Immunodeficiency Virus, Feline Leukemia Virus, *Leptospira* spp, *Mycoplasma haemofelis*, Panleukopenia Virus, *Toxoplasma gondii*, and West Nile Virus.

Canine pathogens include, but are not limited to, Canine Adenovirus, Canine Distemper Virus, Canine Herpesvirus, *Bordetella bronchiseptica*, *Neospora Hughesi* and *Caninum*, *Anaplasma phagocytophilum*, *Rickettsia rickettsii*, *Anaplasma platys*, Canine parainfluenza virus, *Tritrichomonas foetus*, *Clostridium difficle*, *Cryptosporidium* spp., *Cryptosporidium felis*, *Mycobacterium* spp., *Salmonella* spp., *Giardia* spp and *Taenia* spp.

Equine pathogens include, but are not limited to, Equine Herpes Virus, Equine Influenza A, *Lawsonia intracellularis*, *Streptococcus equi*, Equine Arteritis virus, *Campylobacter jejuni*, *E. Coli*, *Shigella* spp., *Yersinia enterocolitica*, *Rhodococcus equi*, West Nile and *Leptospira* spp.

Marine mammal pathogens include, but are not limited to, bacteria: *Staph* sp., *Strep* sp., *Erysipelas rhusiopathiae*, *Bartonella*, *Coxiella*, *Chlamydia*, *Pseudomonas* sp., *Pseudomonas pseudomallei*, *Pseudomonas mallei*, *Klebsiella*, *E. coli*, *Salmonella* sp., *Clostridia perfringens* and *Enterococcus*; viruses: Dolphin pox, seal pox, papilloma universal, papilloma manatee, canine adenovirus, influenza A and B, hepatitis A and B, Bovine enterovirus, Cosackivirus, encephalomyocarditis virus, Morbilliviruses, canine distemper virus, Bovine corona virus, Bovine rotavirus, universal herpes and echovirus; fungi: *Aspergillus, Nocardia, Histoplasma, Blastomyces, Coccidioides immitis, Lacazia loboi, Saksenaea* and *Aphophysomyces*.

Some examples of other analytes that can be detected include pesticides and/or toxins, such as: aflatoxins, arsenic, botulin, ciguatera toxin, cyanide, deoxynivalenol, dioxin, fungi, fumonisins, fusarium toxins, heavy metals, histadine, histamine, lead, marine toxins, mercury, mycotoxins, neurotoxin, nicotine, ochratoxin A toxins, patulin toxins, polychlorinated phenyls, pyrrolizidine alkaloids, ricin, scombrotoxins, shellfish toxin, tetrodotoxin, trichothecenes, zearelenone, and the combinations thereof.

Other target analytes may include food allergens, such as: almond, egg, gliadin, gluten, hazelnut, milk, peanut, soy residues and combinations thereof.

It is also to be understood that, in certain embodiments, the biosensor device can detect analytes over desired time duration. The duration can be a first pre-determined time interval and a least a second pre-determined time interval that are calculated. In certain embodiments, an analyte correlation value is calculated during the test time interval.

EXAMPLES

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Cyclic voltammetry was used for electrochemical characterization of the sensing matrix described herein. Cyclic voltammetry is an electrochemical technique based on electrical current measurement as a function of voltage. The technique involves a working electrode where redox reactions or adsorption occurs, a reference electrode as a constant potential reference, an auxiliary or counter electrode that completes the circuit, an electrolyte, and a potentiostat (voltage source).

Gold circuits deposited on a micro interdigitated electrode acted as a transducer. The sensing matrix comprised a SAM and was formed on a gold electrode as the working electrode. The working electrode, a reference electrode, and a counter electrode were placed in a glass flask that was filled with electrolytes. Voltage was changed at a pre-determined rate and range, and the corresponding current change was recorded.

Figure 8:
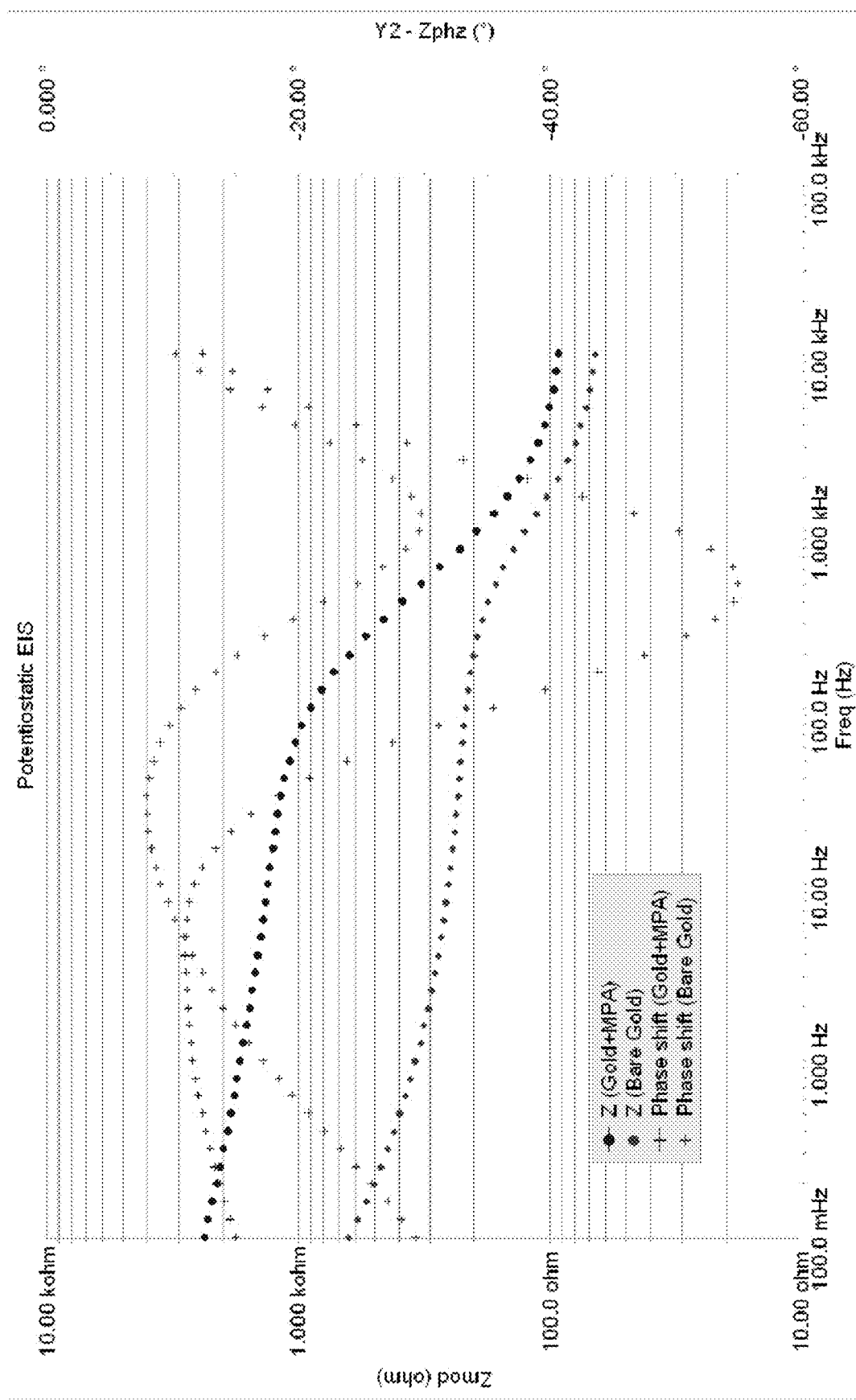
FIG. 8 is a potentiostatic electrochemical impedance spectroscopy (EIS) impedance curve showing a gold electrode with MPA SAM has a higher impedance magnitude and a different phase shift than a bare gold electrode.
Figure 9:
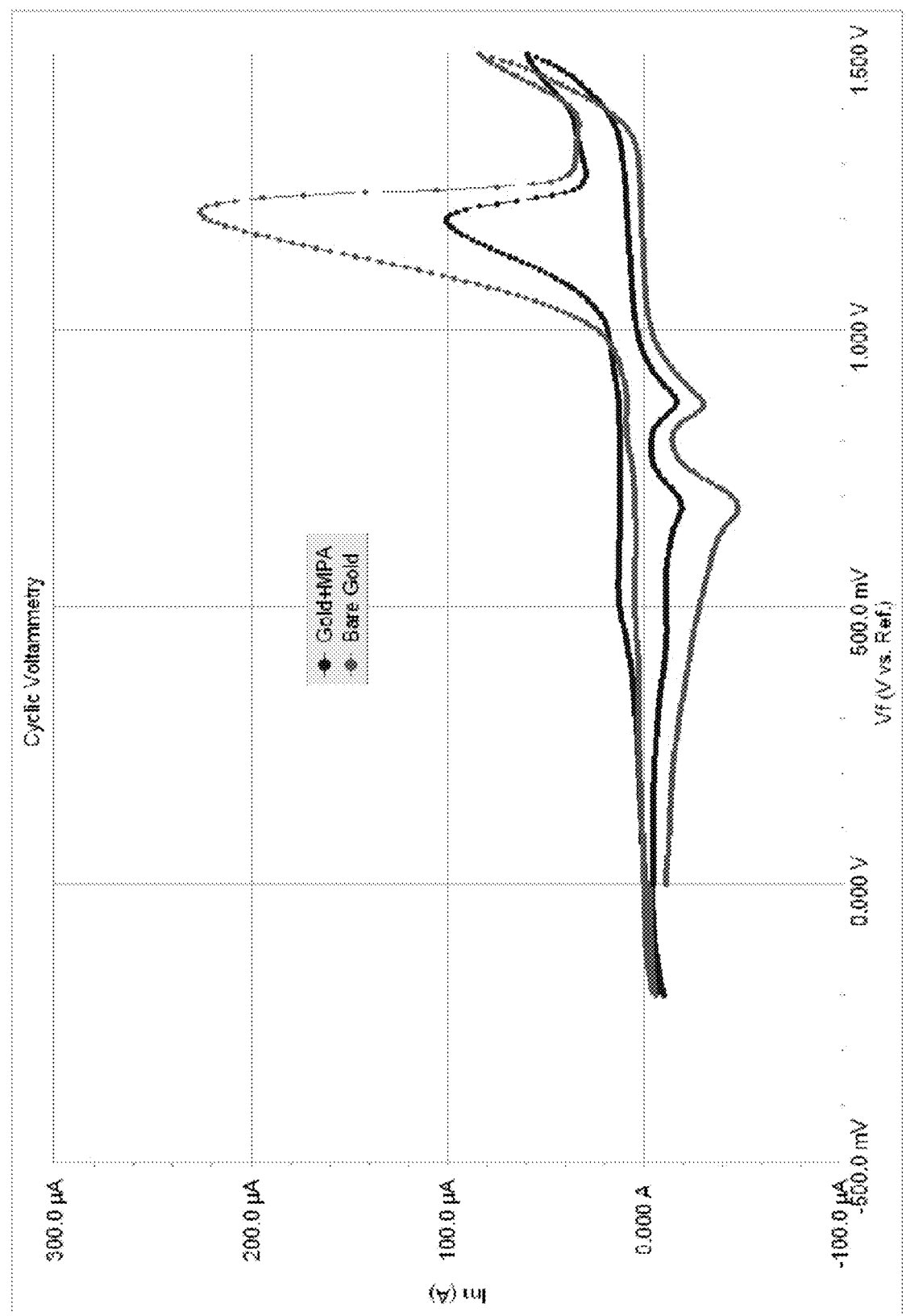
FIG. 9 is a cyclic voltammogram showing that a bare gold electrode has a higher maximum current, and therefore lower resistance, than a gold electrode with MPA SAM.

The gold electrode with SAM was shown to have higher impedance than a bare gold electrode. The gold electrode with MPA SAM was shown to have higher impedance magnitude and a different phase shift than the bare gold electrode. These results are depicted in the impedance curves in FIG. 5 and FIG. 8. Cyclic voltammetry revealed that a bare gold electrode has higher maximum current (lower resistance) than a gold electrode with MPA SAM. The cyclic voltammogram showing this is depicted in FIG. 9.

Figure 10:
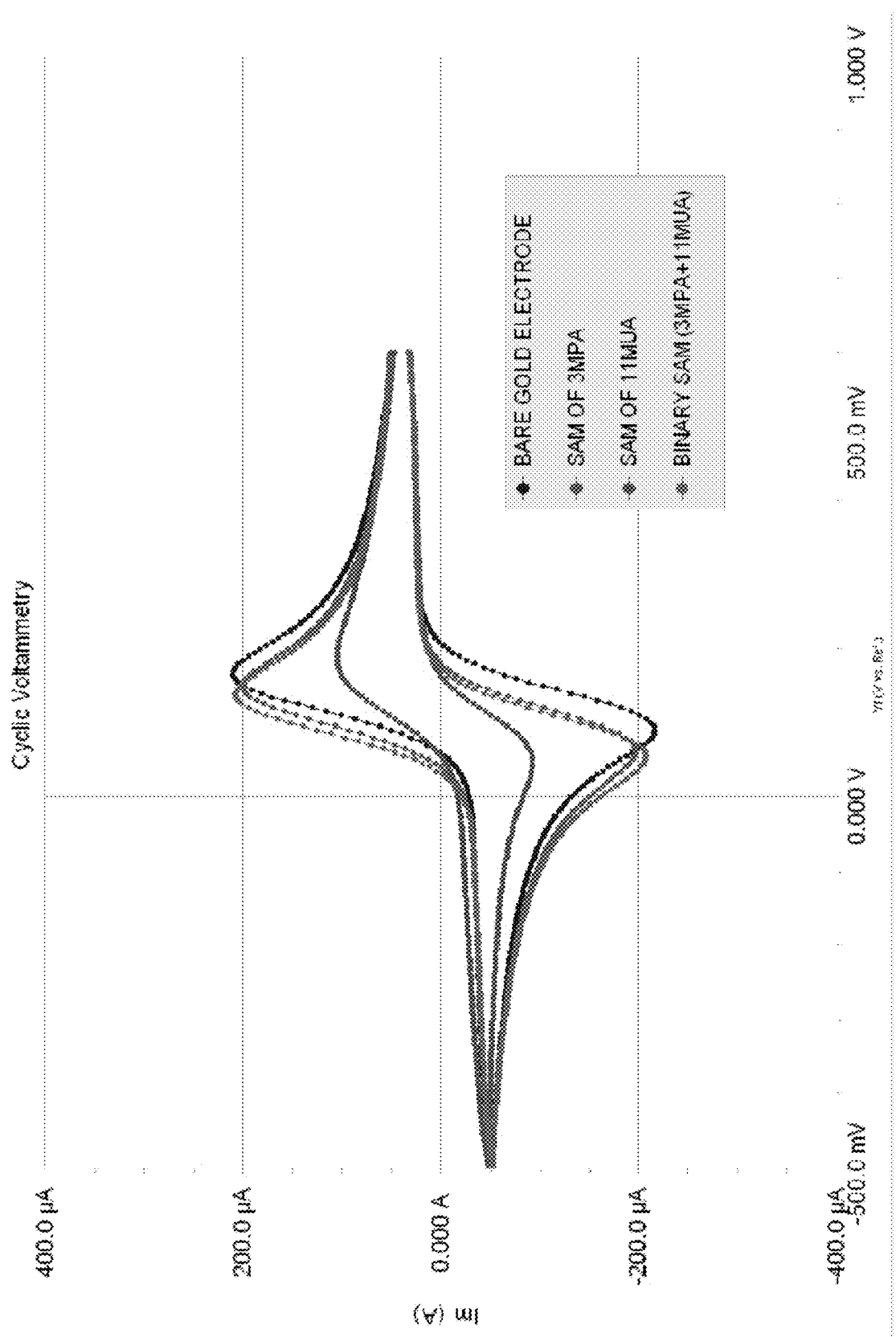
FIG. 10 is a cyclic voltammogram showing a comparison between a bare gold electrode, a gold electrode with 3-MPA SAM, a gold electrode with 3-MPA and 11-MUA SAM, and a gold electrode with 11-MUA SAM. The curves show the gold electrode with 11-MUA SAM has the highest resistance.
Figure 11:
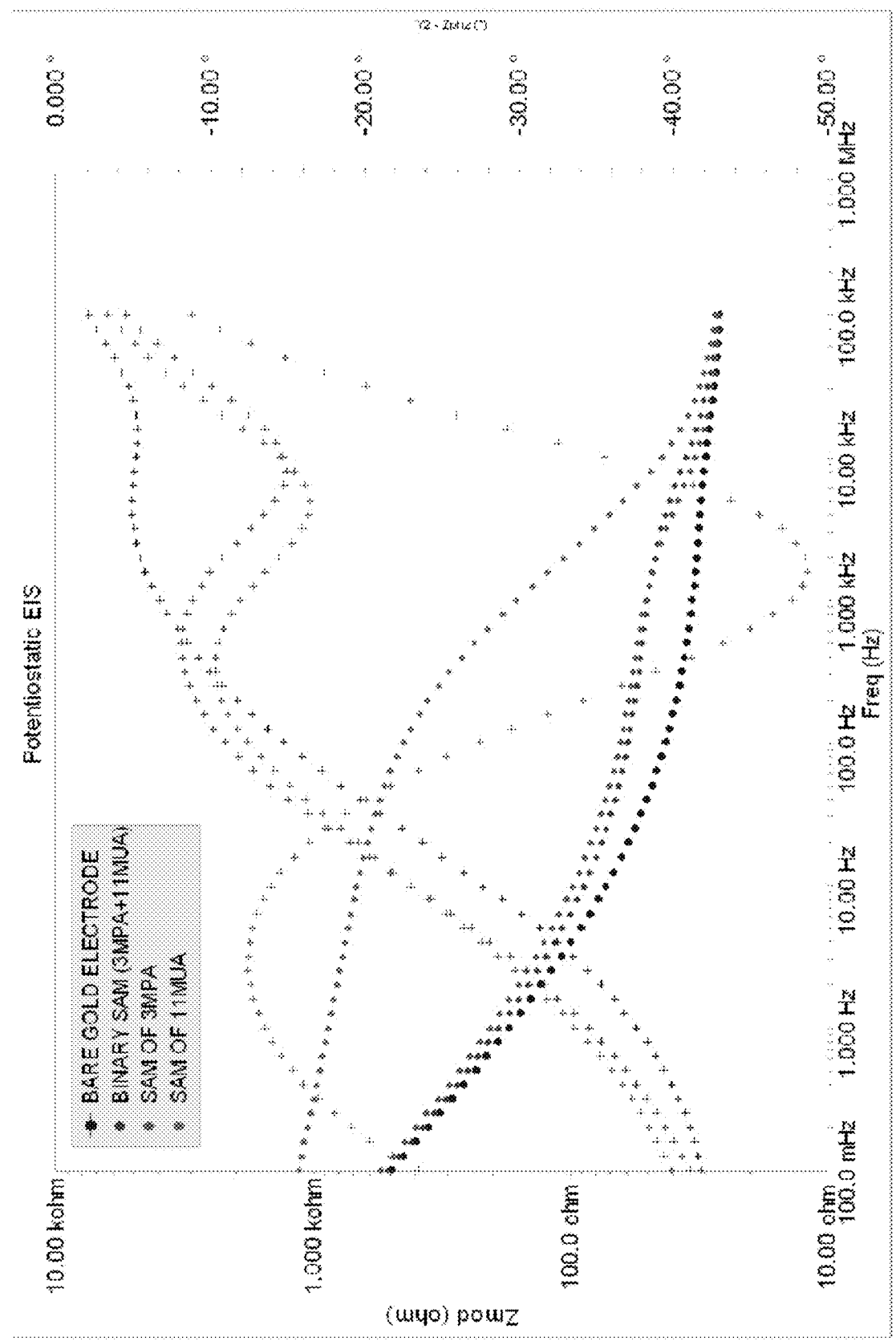
FIG. 11 shows EIS impedance curves for four electrodes: a bare gold electrode, a gold electrode with 3-MPA SAM, a gold electrode with 3-MPA and 11-MUA SAM, and a gold electrode with 11-MUA SAM. The gold electrode with 11-MUA SAM was shown to have the highest impedance and the most distinct phase shift trend.

Different SAMs were tested. Specifically, four electrodes were compared: a bare gold electrode, a gold electrode with 3-MPA SAM, a gold electrode with 3-MPA and 11-MUA SAM, and a gold electrode with 11-MUA SAM. The gold electrode with 11-MUA SAM had not only the highest resistance, but also the highest impedance, and the most different phase shift trend. FIG. 10 and FIG. 11 show these results.

Example 2

Screen printed electrodes (SPE) were sonicated in ethanol (99.5%) for 10 minutes and dried in a desiccator. A SPE was connected to a potentiostat and immersed in a conditioning solution containing 1 mL ammonium acetate buffer in 10 mL $H_2O$. Potential sweeping was performed from 0.6 V to −0.5 V for electrochemical conditioning of the gold electrode surface.

A self-assembled monolayer (SAM) was formed on the SPE gold surface. SPEs were soaked in a solution of 1 mM 11-mercaptoundecanoic acid (MUA) in ethanol for 12 hours and then rinsed with ethanol to remove unbounded 11-MUA molecules. The electrodes were then treated in a solution of 0.05 M 1-ethyl-3-(3-dimethylaminopropyl)carbodiimide (EDC) and 0.2 M N-hydroxysuccinimide (NHS) cross-linkers. After being rinsed and dried, a solution of 20 μg/mL of *Staphylococcus* antibody in a phosphate buffer solution (pH 7.2) was dropped on the electrode surface and then held still for 2 hour. The electrode was then rinsed with a phosphate buffer. In order to decrease non-specific adsorption, a solution of bovine serum albumin (BSA) in the phosphate buffer was used to block unreacted sites of the SAM.

Example 3

Electrochemical impedance spectroscopy (EIS) was performed using the software interface of the potentiostat from 1 Hz to 100 kHz. FIGS. 12-15 show plots of impedance versus frequency.

Figure 12:
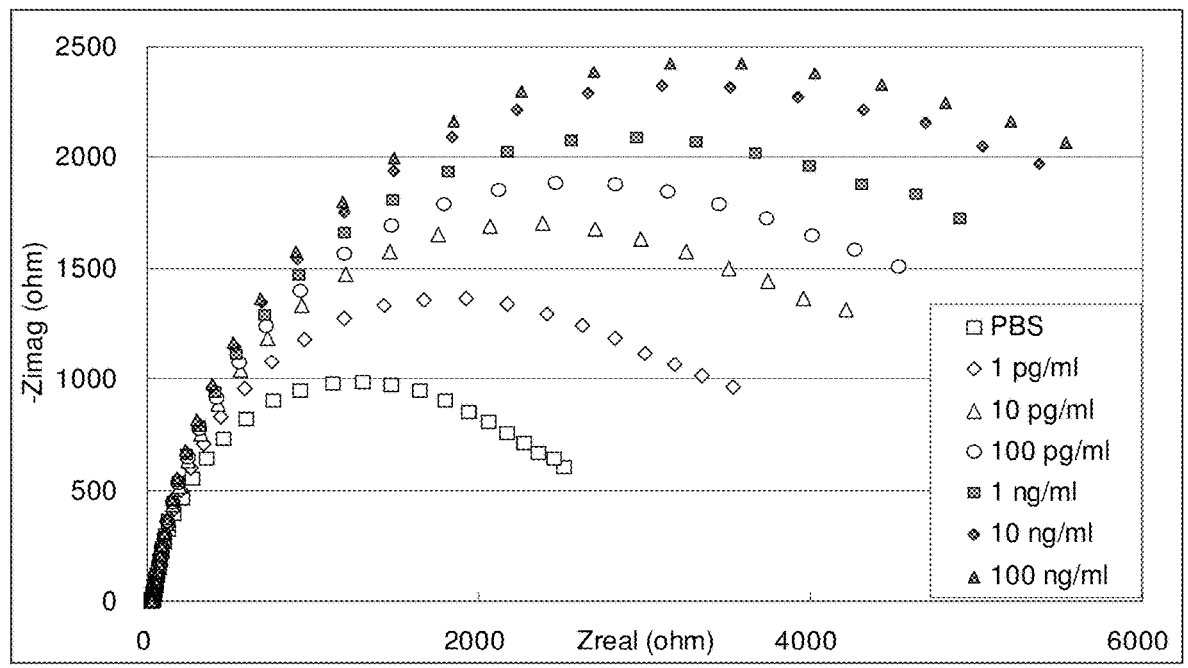
FIG. 12 shows impedance curves generated by the sensing matrix comprising 11-MUA/MRSA antibody when exposed to serial dilutions of purified methicillin-resistant *Staphyloccus aureus* (MRSA) specific protein PBP2a in PBS for 10 minutes.

FIG. 12 shows impedance curves that were generated by the sensing matrix comprising 11-MUA/MRSA antibody when it was exposed to serial dilutions of purified methicillin-resistant *Staphyloccus aureus* (MRSA) specific protein PBP2a in PBS for 10 minutes. The impedance shift was detectable at as low as 1 pg/ml of the protein, thus showing the sensitivity of this embodiment.

Figure 13:
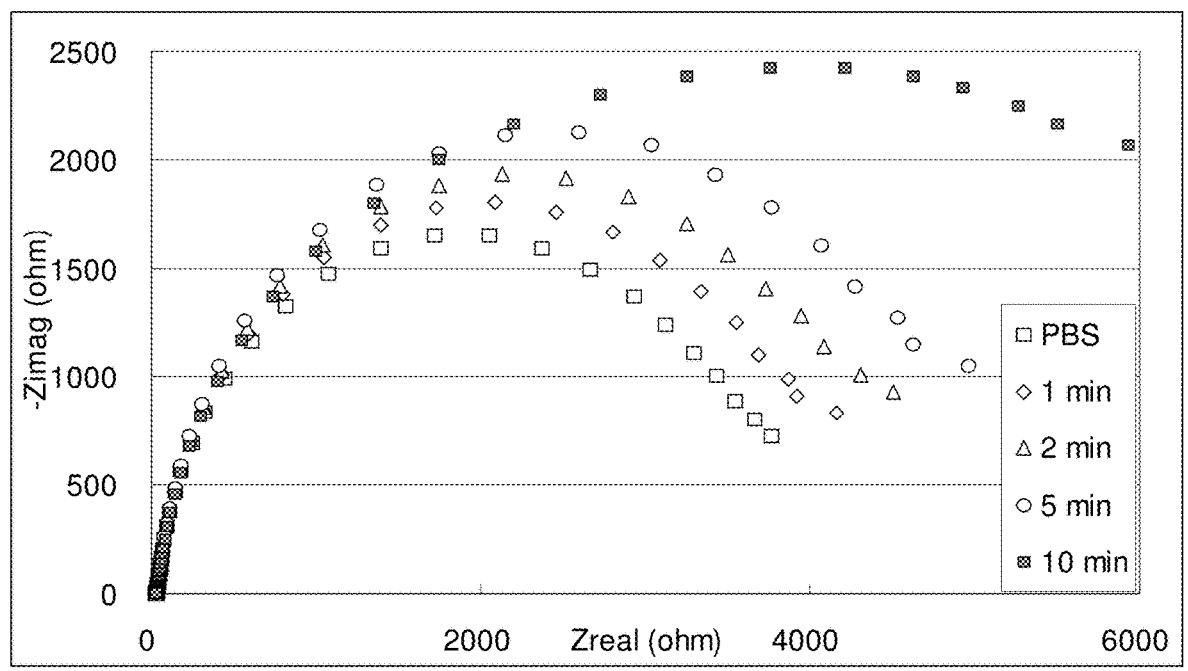
FIG. 13 shows impedance curves generated by the sensing matrix comprising 11-MUA/MRSA antibody when exposed to 1 ng/ml of purified MRSA specific protein PBP2a in PBS for the time periods indicated.

FIG. 13 shows the responding time of the sensing, where the signal can be detected as rapid as in 1 minute after the sensor exposed to the target protein.

Figure 14:
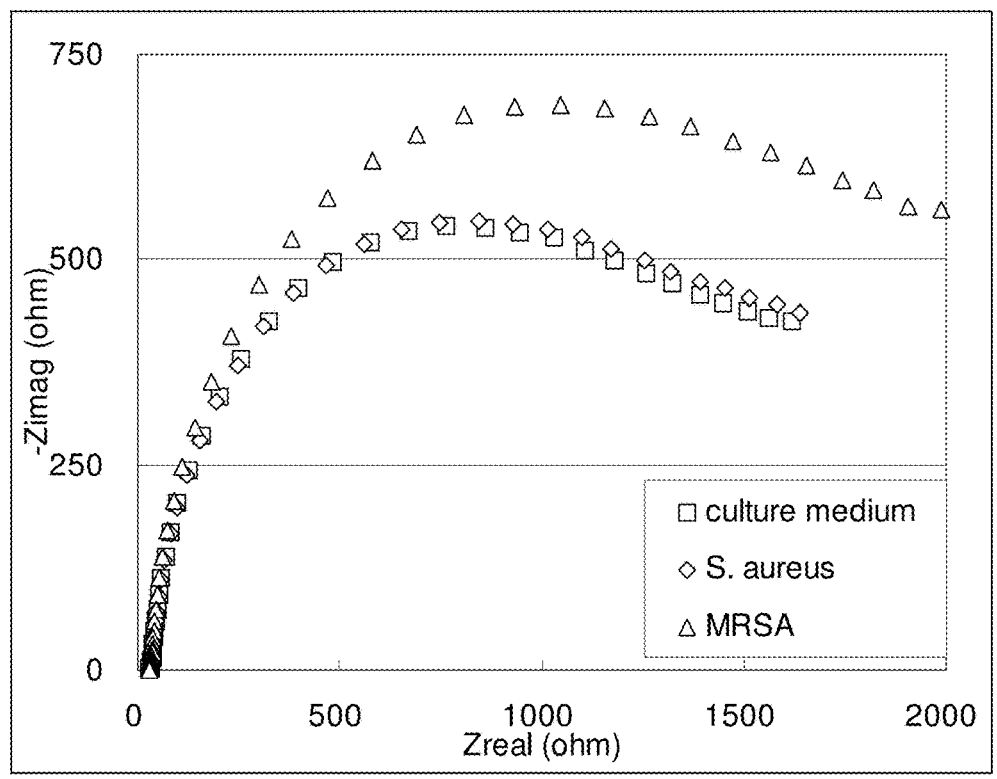
FIG. 14 shows an impedance curve generated by the sensing matrix comprising 11-MUA/MRSA antibody when exposed to the culture of $10^6$ cells/ml MRSA, $10^6$ cells/ml non-resistant *Staphylococcus aureus*, or blank culture medium.

FIG. 14 shows an impedance curve generated by the sensing matrix comprising 11-MUA/MRSA antibody when exposed to the culture of $10^6$ cells/ml MRSA, $10^6$ cells/ml non-resistant *Staphylococcus aureus*, or blank culture medium. A significant shift was observed when MRSA was present.

Figure 15:
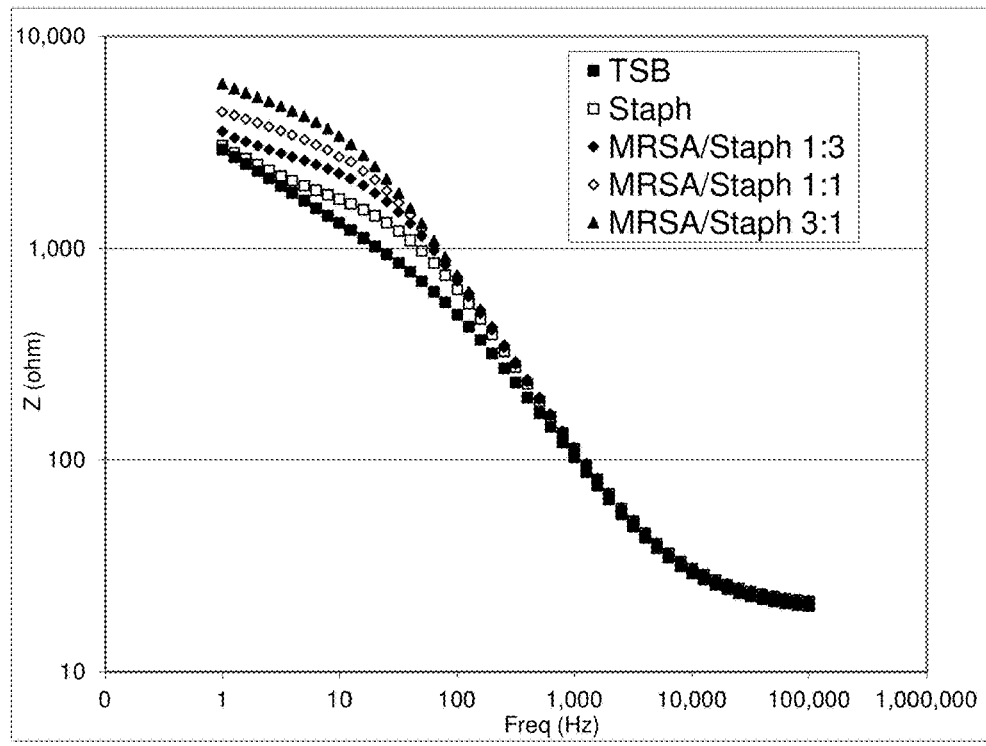
FIG. 15 shows impedance changes when the sensing matrix comprising 11-MUA/MRSA antibody was exposed to a mixture of total $10^6$ cells/ml of MRSA and non-resistant *Staphylococcus aureus*. The shift of the curves corresponded to increased MRSA in the solution.

As shown in FIG. 15, when put in contact with the culture of $10^6$ cells/ml MRSA, $10^6$ cells/ml non-resistant *Staphylococcus aureus*, or blank culture medium, there was a significant shift was observed only when MRSA was present. Furthermore, as shown, in FIG. 15, this sensing method can specifically identify MRSA in a mixture of MRSA and the non-resistant strain. The shift of the curves corresponded to increased MRSA in the solution.

Although a significant change in impedance was not seen within one minute of putting the chip into a bacteria sample, the slope of the impedance-frequency (Z-f) curve changed immediately when MRSA bacteria were present. Thus, the Z-f curve slope, rather than the impedance magnitude itself, can be used as the sensing signal for fast detection.

Example 4

It is to be understood that, depending on the particular embodiment, the biosensor device can utilize any of several principles of detection. In certain other embodiments, the types of signals detected include electrochemical (based on electrical properties), photometric (based on light properties), calorimetric (based on temperature change), and piezoelectric (based on elastic deformation of crystals caused by electrical potential).

Example 5

The biosensor device may also be adapted for use in and/or incorporated into a variety of medical instruments or surgical tools, including but not limited to: endoscopic imaging devices, harvesting devices, retractors such as Hohmann retractors, bone hooks, skin hooks, nerve hooks, tension devices, forceps, elevators, drill sleeves, osteotomes, spinal rongeurs, spreaders, gouges, bone files and rasps, bone awls, rib shears, trephines, suction tubes, taps, tamps, calipers, countersinks, suture passers, and probes.

Example 6

The biosensor device described herein can deliver instantaneous, accurate sensing of a target analyte. In certain embodiments, the biosensor device can be fitted on a medical instrument adapted to check a human throat for the presence of *Streptococcus*. The biosensor device can be used by a physician or other medical personnel to determine whether a patient, such as a child patient, has a *streptococcus* infection by placing the tip of a medical instrument that includes the biosensor into the throat of the patient.

In other embodiments, the biosensor device can be adapted for use in a hip revision procedure, wherein a medical instrument comprising the biosensor device is inserted to check for an infection such as tuberculosis of bone. The biosensor device enables immediate infection detection in any part of the body without having to wait for cultures.

In intraoperative procedure, a method that can sense the infection leading to determination of the following procedure does not exist to date. For example, in hip surgery, the current method still does not give determination of infection. The aspiration of the hip joint has to be shipped to a medical laboratory for evaluation. It will also involve an additional procedure to the patient. Under such circumstances, the surgeon can apply the sensor for the first reading while opening the hit joint for implantation. The second reading can be taken after the implant has been removed. This is the major area where the infection can be present. Use of the biosensor device aids in determining if a temporary implant with antibiotic administration needs to be applied after a wash out or a definite implantation can be done.

Example 7

In clinical practice, for out patients, the infection sensor can be directly brought into contact with infected sites, and the outcome can be read on the display immediately.

In clinical practice, for out patients, the sensor can be used to determine the pathogen on the swab of the infected area.

In day care and clinical practice, it is a standard procedure to take the aspiration of the joint for evaluation. The fluid can be exposed to the sensor on a specially designed syringe device or applied on the biosensor device.

In emerging economies, such as in Southeast Asia, six out of ten patients have TB. This biosensor device is especially useful as a non-invasive instrument to determine the TB infections in real-time.

Certain embodiments and uses of the biosensor device disclosed herein are defined in the examples herein. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A biosensor for detecting the presence of a target analyte in a sample, the biosensor comprising:
   a transducer component comprising an electrode operatively connected to a microprocessor, the microprocessor being adapted to receive, process, and transmit a signal; and,
   a receptor component having:
      i) a sensing element capable of detecting and binding to at least one target analyte present in a sample, and
      ii) a self-assembled monolayer (SAM) layer, the SAM layer being positioned between and in contact with the sensing element and the electrode;
   the transducer component and the receptor component being capable of being brought into direct contact with the sample in situ,
   wherein the sensing element, in the presence of the target analyte present in the sample, causes a detectable signal capable of being transmitted to the electrode via the SAM layer,
   wherein the electrode includes a working electrode component, a reference electrode component, and a counter electrode component, wherein a proximal end of the working electrode component, a proximal end of the reference electrode component, and a proximal end of the counter electrode component are integrated on a first end of the electrode,
   wherein the electrode comprises an annular surface with the working electrode component defining a circular area in the center of the annular surface and the reference electrode component and the counter electrode component each extending a distance around, and at a distance from, the working electrode component in a manner concentric with the working electrode component, and
   the biosensor further includes a domed electrode mesh, wherein a distal end of each of the working electrode component, reference electrode component, and counter electrode component is protected by the domed electrode mesh.

2. The biosensor of claim 1, wherein the biosensor is capable of detecting the presence of the target analyte in real time.

3. The biosensor of claim 1, wherein the sensing element comprises at least one antibody capable of detecting at least one bacterial target analyte.

4. The biosensor of claim 1, wherein the sample comprises a fluid or tissue in a living organism.

5. The biosensor of claim 1, wherein the sample comprises a fluid or tissue in a living organism in vivo.

6. The biosensor of claim 1, wherein the sample comprises a food product.

7. The biosensor of claim 1, wherein the rate and degree of signal change correspond to the presence and concentration of the target analyte.

8. The biosensor of claim 1, wherein the presence of the target analyte is detected by impedance signal.

9. The biosensor of claim 1, wherein the detectable signal comprises a change in impedance as a function of frequency.

10. The biosensor device of claim 1, wherein the microprocessor is configured to screen noise and to pick up impedance change at a frequency range from about 1 Hz to about 10 Hz.

11. The biosensor of claim 1, wherein the presence of the target analyte is detected by amperometric signal.

12. The biosensor of claim 1, wherein the electrode comprises a micro-interdigitated gold electrode.

13. The biosensor of claim 1, wherein the detectable signal is displayed on a display by the microprocessor through radio frequency identification (RFID) communication.

14. The biosensor of claim 1, wherein the biosensor is integrated into a medical, dental, or veterinary device having a tissue-contacting surface.

15. The biosensor of claim 1, wherein the target analyte comprises a pathogen selected from the group consisting of: *Staphylococcus aureaus*, methicillin-resistant *Staphylococcus aureus* (MRSA), *Streptococcus pyogenes, Streptococcus pneuomoniae, Streptococcus agalactiae, Staphylococcus epidermis, Staphylococcus saprophyticus, Escherichia coli, Legionella pneumophila, Pseudomonas aeruginosa, Enterococcus faecalis, Listeria, Cyclospora, Salmonella enteritidis, Helicobacter pylori, Tubercle bacillus* (TB), other *Bacillus, Clostridium botulinum, Clostridium difficile, Clostridium perfringens, Clostridium tetani, Sporohalobacter, Anaerobacter, Heliobacterium, Brucella abortus, Brucella canis, Brucella melitensis, Brucella suis, Cyanobacteria*, green sulfur bacteria, *Chloroflexi*, purple bacteria, *thermodesulfobacteria, hydrogenophilaceae, nitrospirae, Burkholderia cenocepacia, Mycobacterium avium, Mycobacterium leprae, Mycobacterium tuberculosis, Mycobacterium ulcerans, Lactobacillus, Lactococcus, Bordetella pertussis, Chlamydia pneumoniae, Chlamydia tracomatis, Chlamydia psittaci, Borrelia burgdorferi, Campylobacter jejuni, Francisella tularensis, Leptospira monocytogenes, Leptospira interrogans, Mycoplasma pneumoniae, Rickettsia rickettsii, Shigella sonnei, Traponema pallidum, Vibrio cholerae, Haemophilus influenzae, Neiserria meningitidis, Yersinia pestis, Bartonella henselae, Borrelia burgdorferi, Chlamydia psittaci, Dirofilaria immitis, Ehrlichia canis,* Feline Calicivirus, Feline Coronavirus, Feline Herpesvirus, Feline Immunodeficiency Virus, Feline Leukemia Virus, *Leptospira* spp., *Mycoplasma haemofelis*, Panleukopenia Virus, *Toxoplasma gondii*, West Nile Virus, Canine Adenovirus, Canine Distemper Virus, Canine Herpesvirus, *Bordetella bronchiseptica, Neospora Hughesi, Neospora Caninum, Anaplasma phagocytophilum, Rickettsia rickettsii, Anaplasma platys,* Canine parainfluenza virus, *Tritrichomonas foetus, Cryptosporidium* spp., *Cryptosporidium felis, Mycobacterium* spp., *Salmonella* spp., *Giardia* spp., *Taenia* spp, Equine Herpes Virus, Equine Influenza A, *Lawsonia intracellularis, Streptococcus equi*, Equine Arteritis virus, *Shigella* spp., *Yersinia enterocolitica, Rhodococcus equi,* West Nile, *Leptospira* spp, *Erysipelas rhusiopathiae, Bartonella, Coxiella, Pseudomonas* sp., *Pseudomonas pseudomallei, Pseudomonas mallei, Klebsiella, Salmonella* sp., *Enterococcus*, Dolphin pox, seal pox, papilloma universal, papilloma manatee, canine adenovirus, influenza A and B, hepatitis A and B, Bovine enterovirus, Cosackivirus, encephalomyocarditis virus, Morbilliviruses, canine distemper virus, Bovine corona virus, Bovine rotavirus, universal herpes, echovirus, *Aspergillus, Nocardia, Histoplasma, Blastomyces, Coccidioides immitis, Lacazia loboi, Saksenaea*, and *Aphophysomyces*.

16. The biosensor of claim 1, wherein the receptor binds to a target analyte selected from the group consisting of: pesticides, toxins, aflatoxins, arsenic, botulin, ciguatera toxin, cyanide, deoxynivalenol, dioxin, fungi, fumonisins, fusarium toxins, heavy metals, histadine, histamine, lead, marine toxins, mercury, mycotoxins, neurotoxin, nicotine, ochratoxin A toxins, patulin toxins, polychlorinated phenyls, pyrrolizidine alkaloids, ricin, scombrotoxins, shellfish toxin, tetrodotoxin, trichothecenes, zearelenone, and the combinations thereof.

17. The biosensor of claim 1, wherein the SAM comprises mercaptoproprionic acid (MPA), 11-mercaptoundecanoic acid (MUA), 1-tetradecanethiol (TDT), or dithiobios-N-succinimidyl propionate (DTSP).

18. The biosensor of claim 1, wherein the domed electrode mesh protects only the distal ends of each of the working electrode component, reference electrode component, and counter electrode component.

19. The biosensor of claim 1, wherein the domed electrode mesh surrounds the distal ends of each of the working electrode component, reference electrode component, and counter electrode component.

20. A method of making a biosensor capable of detecting a target analyte in situ in a sample, comprising:
linking a sensing element comprising antibodies to an electrode via a self-assembled monolayer (SAM); and
operatively connecting a microprocessor to the electrode such that, when the sensing element binds to a target analyte present in situ in a sample, the microprocessor detects and transmits a signal,
wherein the electrode includes a working electrode component, a reference electrode component, and a counter electrode component, wherein a proximal end of the working electrode component, a proximal end of the reference electrode component, and a proximal end of the counter electrode component are integrated on a first end of the electrode;
wherein the electrode comprises an annular surface with the working electrode component defining a circular area in the center of the annular surface and the reference electrode component and the counter electrode component each extending a distance around, and at a distance from, the working electrode component in a manner concentric with the working electrode component; and
the biosensor includes a domed electrode mesh, wherein a distal end of each of the working electrode component, reference electrode component, and counter electrode component is protected by the domed electrode mesh.

21. The method of claim 20, further comprising the step of: configuring the biosensor on a medical instrument from the group consisting of: endoscopic imaging devices, harvesting devices, retractors, bone hooks, skin hooks, nerve hooks, tension devices, forceps, elevators, drill sleeves, osteotomes, spinal rongeurs, spreaders, gouges, bone files and rasps, bone awls, rib shears, trephines, suction tubes, taps, tamps, calipers, countersinks, suture passers, and probes.

22. The method of claim 20, further comprising using electrochemical impedance to detect and/or quantify the target analyte.

23. The method of claim 20, wherein the microprocessor includes an algorithm program capable of screening background noise and detecting an impedance signal that represents the presence and concentration of target analyte.

24. A method of detecting a bacterial infection in a living organism, comprising:
   placing the biosensor of claim 1 at least partially in or on the living organism sufficient to come into contact with any bacterial target analyte present in the living organism; and,
   detecting the presence of the bacterial target analyte when the biosensor device transmits the detectable signal.

25. The method of claim 24, wherein the biosensor device determines whether the bacterial target analyte is Gram-positive or Gram-negative, and the biosensor device transmits a signal indicating whether the bacterial target analyte is Gram-positive or Gram-negative.

\* \* \* \* \*